US010308987B2

(12) United States Patent
Parr et al.

(10) Patent No.: US 10,308,987 B2
(45) Date of Patent: *Jun. 4, 2019

(54) 3.4 KB MITOCHONDRIAL DNA DELETION FOR USE IN THE DETECTION OF CANCER

(71) Applicant: MDNA Life Sciences Inc., Wilmington, DE (US)

(72) Inventors: Ryan L. Parr, Thunder Bay (CA); Robert Thayer, Thunder Bay (CA); Gabriel D. Dakubo, Thunder Bay (CA); Jennifer Creed, Broomfield, CO (US); Kerry Robinson, Thunder Bay (CA); Andrea Maggrah, Thunder Bay (CA); Brian Reguly, Thunder Bay (CA)

(73) Assignee: MDNA Life Sciences Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,175

(22) Filed: Mar. 27, 2017

(65) Prior Publication Data

US 2018/0010193 A1 Jan. 11, 2018

Related U.S. Application Data

(63) Continuation of application No. 14/874,155, filed on Oct. 2, 2015, now abandoned, which is a continuation of application No. 14/507,027, filed on Oct. 6, 2014, now abandoned, which is a continuation of application No. 12/748,120, filed on Mar. 26, 2010, now abandoned, which is a continuation-in-part of application No. 11/975,390, filed on Oct. 18, 2007, now Pat. No. 8,008,008, which is a continuation of application No. PCT/CA2006/000652, filed on Apr. 18, 2006, said application No. 12/748,120 is a continuation of application No. PCT/CA2007/001711, filed on Sep. 26, 2007.

(60) Provisional application No. 60/672,016, filed on Apr. 18, 2005, provisional application No. 60/721,522, filed on Sep. 29, 2005, provisional application No. 60/789,872, filed on Apr. 7, 2006.

(51) Int. Cl.
C12Q 1/68 (2018.01)
C12Q 1/6886 (2018.01)
G01N 33/574 (2006.01)

(52) U.S. Cl.
CPC ..... *C12Q 1/6886* (2013.01); *G01N 33/57415* (2013.01); *G01N 33/57434* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,565,323 | A | 10/1996 | Parker et al. |
| 6,344,322 | B1 | 2/2002 | Polyak et al. |
| 8,008,008 | B2 * | 8/2011 | Parr et al. ..................... 435/6.12 |
| 2002/0155438 | A1 | 10/2002 | Simpson et al. |
| 2003/0092019 | A1 | 5/2003 | Meyer et al. |
| 2004/0191769 | A1 | 9/2004 | Marine et al. |
| 2005/0026167 | A1 | 2/2005 | Birch-Machin et al. |
| 2005/0244851 | A1 | 11/2005 | Blume |

FOREIGN PATENT DOCUMENTS

| CA | 2356536 | 2/2003 |
| EP | 0812922 | 12/1997 |
| EP | 1 266 970 | 12/2002 |
| JP | 11-113597 | 4/1999 |
| WO | WO 98/23632 | 6/1998 |
| WO | WO 00/63441 | 10/2000 |
| WO | WO 01/68923 | 9/2001 |
| WO | WO 02/22873 | 3/2002 |

(Continued)

OTHER PUBLICATIONS

Harbottle and Ma Birch-Machin A. "Real-time PCR analysis of a 3895 bp mitochondrial DNA deletion in nonmelanoma skin cancer and its use as a quantitative marker for sunlight exposure in human skin," British Journal of Cancer, Nature Publishing Group, London, GB, vol. 94, No. 12, Jan. 1, 2006 (Jan. 1, 2006), pp. 1887-1893.
Linnane, Anthony W. et al., Mitochondrial Gene Mutation: The Ageing Process and Degenerative Diseases, 22 Biochemistry International. pp. 1067-1076 (1990).
Modica-Napolitano, Josephine S. et al., Mitochondria as Targets for Detection and Treatment of Cancer, 4 Expert Reviews in Molecular Medicine. pp. 1-19 (2002).
Taanman, J.W. et al., Molecular Mechanisms in Mitochondrial DNA Depletion Syndrome, 6 Human Molecular Genetics. pp. 935-942 (1997).
Ward, R.H. et al., Genetic and Linguistic Differentiation in the Americas, 90 Proceedings of the National Academy of Sciences. pp. 10663-10667 (1993).

(Continued)

*Primary Examiner* — James Martinell
(74) *Attorney, Agent, or Firm* — Simpson & Simpson, PLLC

(57) ABSTRACT

A method for detecting cancer in an individual comprising detecting a deletion in the nucleic acid sequence between residues 10743 and 14125 in mitochondrial DNA, obtaining a biological sample from the individual, extracting the mitochondrial DNA (mtDNA) from the sample, quantifying the amount of mtDNA in the sample having a deletion in the nucleic acid sequence between residues 10743 and 14125 of the mtDNA genome, and comparing the amount of mtDNA in the sample having the deletion to at least one known reference sample.

17 Claims, 7 Drawing Sheets

Specification includes a Sequence Listing.

(56) References Cited

FOREIGN PATENT DOCUMENTS

| WO | WO 02/101086 | 12/2002 |
|---|---|---|
| WO | WO 03/078661 | 9/2003 |
| WO | WO 06/11029 | 10/2010 |

OTHER PUBLICATIONS

Kajander, Olli A., Anja T. Rovio, Kari Majamaa, Joanna Poulton, Johannes N. Spelbrink, Ian J. Holt, Pekka J. Karhunen and Howard T. Jacobs, Human mtDNA sublimons resemble rearranged mitochondrial genoms found in pathological states, Sep. 25, 2000, pp. 2821-2835, vol. 9, No. 19, Human Molecular Genetics, Oxford University Press.
Chuanzhong Ye et al., Quantitative analysis of mitrochondrial DNA 4977-bp deletion in sporadic breast cancer and benign breast diseases. Breast Cancer Research and Treatment, vol. 108, No. 3, May 31, 2007 (May 31, 2007), pp. 427-434, XP002591332. ISSN: 0167-6806.
Tan, Duan-Jun et al., Comprehensive scanning of somatic mitochondrial DNA mutations in breast cancer. Cancer Research, vol. 62, No. 4, Feb. 15, 2002 (Feb. 15, 2002), pp. 972-976, XP002591333. ISSN: 0008-5472.
Armstrong, B.K. (2004). How sun exposure causes skin cancer: an epidemiological perspective. In Prevention of Skin Cancer, Hill, D., Elwood, J.M. & English, D.J. (eds), vol. 3. pp. 89-116. Cancer Prevention Cancer Causes. Kluwer Acedemic Publishers.
Armstrong, B.K. & Kricker, A. (2001). The epidemiology of UV induced skin cancer. J Photochem Photobiol B, 63, 8-18.
Berneburg, M., Gattermann, N., Stege, H., Grewe, M., Vogelsang, K., Ruzicka, T. & Krutmann, J. (1997). Chronically ultraviolet-exposed human skin shows a higher mutation frequency of mitochondrial DNA as compared to unexposed skin and the hematopoietic system. Photochem Photobiol, 66, 271-5.
Berneburg, M., Plettenberg, H., Medve-Konig, K., Pfahlberg, A., Gers-Barlag, H., Gefeller, O. & Krutmann, J. (2004). Induction of the photoaging-associated mitochondrial common deletion in vivo in normal human skin. J Invest Dermatol, 122, 1277-83.
Boukamp, P., Petrussevska, R.T., Breitkreutz, D., Hornung, J., Markham, A. & Fusenig, N.E. (1988). Normal keratinization in a spontaneously immortalized aneuploid human keratinocyte cell line. J Cell Biol, 106, 761-71.
Croteau, D.L. & Bohr, V.A. (1997). Repair of oxidative damage to nuclear and mitochondrial DNA in mammalian cells. JBiol Chem, 272, 25409-12.
Degoul, F., Nelson, I., Amselem, S., Romero, N., Obermaier-Kusser, B., Ponsot, G., Marsac, C. & Lestienne, P. (1991). Different mechanisms inferred from sequences of human mitochondrial DNA deletions in ocular myopathies. Nucleic Acids Res, 19, 493-6.
Durham, S.E., Krishnan, K.J., Betts, J. & Birch-Machin, M.A. (2003). Mitochondrial DNA damage in non-melanoma skin cancer. Br J Cancer, 88, 90-5.
Koch, H., Wittern, K.P. & Bergemann, J. (2001). In human keratinocytes the Common Deletion reflects donor variabilities rather than chronologic aging and can be induced by ultraviolet A irradiation. J Invest Dermatol, 117, 892-7.
Ledoux, S.P., Patton, N.J., Avery, L.J. & Wilson, G.L. (1993). Repair of N-methylpurines in the mitochondrial DNA of xeroderma pigmentosum complementation group D cells. Carcinogenesis, 14, 913-7.
Mita, S., Rizzuto, R., Moraes, C.T., Shanske, S., Arnaudo, E., Fabrizi, G.M., Koga, Y., Dimauro, S. & Schon, E.A. (1990). Recombination via flanking direct repeats is a major cause of large-scale deletions of human mitochondrial DNA. Nucleic Acids Res, 18, 561-7.
Moraes, C.T., Ricci, E., Petruzzella, V., Shanske, S., Dimauro, S., Schon, E.A. & Bonilla, E. (1992). Molecular analysis of the muscle pathology associated with mitochondrial DNA deletions. Nat Genet, 1, 359-67.
Moraes, C.T., Sciacco, M., Ricci, E., Tengan, C.H., Hao, H., Bonilla, E., Schon, E.A. & Dimauro, S. (1995). Phenotype-genotype correlations in skeletal muscle of patients with mtDNA deletions. Muscle & Nerve, 3, S 150-3.
Schon, E.A., Rizzuto, R., Moraes, C.T., Nakase, H., Zeviani, M. & Dimauro, S. (1989). A direct repeat is a hotspot for large-scale deletion of human mitochondrial DNA. Science, 244, 346-9.
Sciacco, M., Bonilla, E., Schon, E.A., Dimauro, S. & Moraes, C.T. (1994). Distribution of wild-type and common deletion forms of mtDNA in normal and respiration-deficient muscle fibers from patients with mitochondrial myopathy. Hum Mol Genet, 3, 13-9.
Shoffner, J.M., Lott, M.T., Voljavec, A.S., Soueidan, S.A., Costigan, D.A. & Wallace, D.C. (1989). Spontaneous Kearns-Sayre/chronic external ophthalmoplegia plus syndrome associated with a mitochondrial DNA deletion: a slip-replication model and metabolic therapy. Proc Natl Acad Sci USA, 86, 7952-6.
Alonso, A. C Alves, M.P. Suarez-Mier, C Albarran, L Pereira, L Fernandez De Simon, P. Martin, O Garcia, L Gusmao, M Sancho, A Amorim 2005. J Clin Pathology 58: 83-86.
Anderson S, et al., Sequence and Organization of the human mitochondrial genomre. Nature 290:457-464, 1981.
Andrews RM, et al., Reanalysis and revision of the Cambridge references sequence for human mitochondrial DNA. Nature Genetics 23(2):147, 1999.
Berneburg M, et al., Singlet oxygen mediates the UVA-induced generation of the photoaging-associated mitochondrial common deletion. J. Biol. Chem. 274(22):15345-15349, 1999.
Berthon P, Valeri A, Cohen-Akeninc A, Drelon E, Paiss T, Wohr G, Latil A et al., Predisposing gene for early-onset prostate cancer, localized on chromosome. 1q42.2-43. Am. J. Hum. Genet., 62: 1416-1424, 1998.
Birch-Machin MA, et al., Study of skeletal muscle mitochondrial dysfunction. Methods in Toxicology, vol. 2, 51-69,1993.
Birch-Machin MA, et al., Mitochondrial DNA deletions in human skin reflect photo rather that chronologic aging. J. Invest.Dermatol 110:149-152 1998.
Birch-Machin MA, Taylor RW, Cochran B, Ackrell BAC, Tumbull DM. Late-onset optic atrophy ataxia, and myopathy associated with a mutation of a complex II gene. Ann Neurol 48: 330-335, 2000(b).
Birch-Machin MA, Mitochondria and skin disease. Clin. Exp. Dermatol,. 25(2), 141-146, 2000 (c).
Birch-Machin MA and Krishnan K. Abstracts—Mitochondria 2001 Meeting San Diego, CA, Feb. 28-Mar. 2, 2001, 1, p. 45 (2001), p. 46.
Birch-Machin MA, Lindsey J. Lusher M and Krishnan K. Mitochondrion1, 1 (Suppl) 1, S30 (2001).
Bogliolo, M, et al., Detection of the 4977 bp mitochondrial DNA deletion in human atherosaclerotic lesions Mutagenesis, 14: 77-82, 1999.
Brierley EJ, Johnson MA, Lightowlers RN, James O, Turnbull DM., Role of mitochondrial DNA mutations in human aging: Implications for the central nervous system and muscle. Ann Neurol 43(2):217-223, 1998.
Brockington, et al., A tandem duplication in the D-loop of human mitochondrial DNA is associated with deletions in mitochondrial myopathies. Nature Genet 4:67-71, 1993.
Brown, M.D., et al., Clustering of Caucasian Leber hereditary optic neuropathy patients containing the 11778 or 14484 mutations on mtDNA lineage. Am J. Humn Genet, 60: 381-387, 1997.
Buttyan R, Sawczuk IS, Benson MC, Siegal JD, Olsson CA., Enhanced expression of the c-myc protooncogene in high grade human prostate cancer. Prostate 11:327-337, 1987.
Cairns P, Okami K, Halachmi S, Halachmi N, Esteller M, Herman JG, Jen J et al., Frequent inactivation of PTEN/MMAC1 in primary prostate cancer. Cancer Res 57:4997-5000, 1997.
Chinnery PF, Howel N, Turnbull DM. Clinical mitochondrial genetics. J. Med. Genet.; J.Med.Genet.; 36: 425-436, 1999.
Chinnery PF and Turnbull DM., Mitochondrial DNA and disease. Lancet 354 (supplement 1): 17-21, 1999.
Cormier-Daire et al., Mitochondrial DNA rearrangements with onset as chronic diarrhea with villous atrophy, The Journal of Pediatrics, Jan. 1994, vol. 124, No. 1, pp. 63-70.

(56) References Cited

OTHER PUBLICATIONS

Chomyn A, et al., Melas mutation in mtDNA binding-site for transcription termination factor causes defects in protein-synthesis and in respiration but no change in levels upstream and downstream mature transcripts. Proc. Natl. Acad. Sci. USA 89(10):4221-4225, 1992.
Corral-Debrinski et al., Association of Mitrochondrial-DNA Damage with aging and coronary atheroscolerotic heart-disease. Mutat Res, 275: 169-180, 1992.
Cortopassi G. A. and Arnheim, N. Detection of a specific mitochondiral DNA deletion in tissues of older humans, Nucleic Acids Research. 18, 6927-6933 1990.
Cortopassi G, Wang E., Modelling the effects of age-related mtDNA mutation accumulation-complex-I deficiency, superoxide and cell-death. Biochim Biophys Acta 1271(1):171-176,1995.
Croteau DL, Stierum RH, Bohr VA, Mitrochondrial DNA repair pathways. Mutat Res 434(3):137-148, 1999.
Easton RD, Merriwether AD, Crews DE, and Ferrell RE., mtDNA varation in the Yanomami Evidence for additional New World founding lineages. Am. J. Hum. Genet. 59:213-225, 1996.
Fahn H, Wang L, Hseith R, Chang S, Kao S, Huang M, and Wei Y. Age-related 4977 bp Deletion in Human Lung Mitochondrial DNA. American Journal of Respiratory Critical Care Medicine, 154:1141-1145, 1996.
Finegold D., Diagnosis: The Promise of DNA Analysis in Understanding Mitrochondrial Disease; Mitochondrial and Metabolic Disorders, p. 12, 1997.
Flanagan N, et al., Pleiotropic effects of the melanocortin 1 receptor (MC1R) gene on human pigmentation. Hum Mol Genet 9 (17):2531-2537, 2000.
Petros, John A. et al., mtDNA mutations increase tumorigenicity in prostate cancer, PNAS, Jan. 18, 2005, vol. 102, No. 3, pp. 719-724.
Flanagan N, Ray AJ, Todd C, Birch-Machin MA and Rees JL. The relation between melanocortin 1 receptor genotype and experimentally assessed ultraviolet radiation sensitivy. J Invest. Dermatol (2001) 117 (5) 1314-1317.
Gattermann, N, Berneburg, M, Heinisch, J, Aul, C, Schneider, W., Detection of the ageing-associated 5-kb common deletion of mitrochondrial-DNA in blood and bone marrow of hematologycally normal adults-absence of the deletion in clonal bone marrow disorders. Leukemia 9(10): 1704-10, 1995.
Habano W, Nakamura S, Sugai T., Microsatellite instability in the mitochondrial DNA of colorectal carcinomas: Evidence for mismatch repair systems in mitrochondrial genome, Oncogene 17 (15):1931-1937, 1998.
Harding RM, et al., Evidence for variable selective pressures at MC1R. Am. J. Hum. Genet. 66, 1351-1361, 2000.
Hattori et al, Age-dependant increase in deleted mitochondrial DNA in the human heart: possible contributory factor to presbycardia, Am. Heart J., 121, 1735-1742, 1991.
Hayashi J, Ohta S, Kikuchi A, Takemitsu M, Goto Y, Nonaka I., Introduction of disease-related mitrochondrial-DNA deletions into hela-cells lacking mitrochondrial-DNA results in mitrochondrial dysfunction. Proc Natl Aced Sci USA 88 (23):10614-10618, 1991.
Hayward SW, Grossfeld GD, Tlsty TD, Cunha GR., Genetic and epigenetic influences in prostatic carcinogenesis—(Review). Int J Oncol 13:35-47, 1998.
Healy E, Birch-Machin MA, Rees JL. Chapter 11. The Human Melanocortin 1 Receptor Gene. In the Melanocortin Receptors (Cone RD (ed)). Humana Press Inc. New Jersey, USA, 1999, p. 341.
Healy E, et al. Melanocortin-1-receptor gene and sun sensitivity in individuals without red hair. Lancet 355. 9209, 1072-1073, 2000.
Hsieh, RH, et al., Age-Dependent Respiratory Function Decline and DNA Deletions in Human Muscle Mitrochondria, Biochemistry and Molecular Biology Int'l, vol. 32, No. 6, Apr. 1994, pp. 1009-1022.
Ikebe et al., Increase of deleted mitochondrial DNA in the striatum in Parkinson's disease and senescence, Biochem. Biophys. Res. Commun. 170, 1044-1048, 1990.
Katayama et al., Deleted mitochondrial DNA in the skeletal muscle of aged individuals, Biochem. Int., 25, 4756 1991.

Kleinle S, et al., Detection and characterization of mitrochondrial DNA rearrangements in Pearson and Kearns-Sayre syndromes by PCR. Human Genet. 100:643-650, 1997.
Konishi N, Cho M, Yamamoto K, Hiasa Y. Genetic changes in prostate cancer. Pathol. Int. 47:735-747, 1997.
Krishnan K and Birch-Machin MA. British Society for Investigative Dermatology Annual Meeting. British Journal of Dermatology (2002), 146, (p. 723).
Ledoux SP, et al. Repair of alkylation and oxidative damage in mitochondrial DNA. Mutat Res 434(3):149-159, 1999.
Lee HC, et al. Ageing-associated tandem duplications in the D-loop of mitochondrial DNA of human muscle. FEBS Letters 354:79-83, 1994.
Lee HC, Lu CY, Fahn HJ, Wei YHu. Aging-and smoking-associated alteration in the relative content of mitochondrial DNA in human lung. Federation of European Biochemical Societies, 441:292-296, 1998.
Lee HC, et al. Concurrent increase of oxidative DNA damage and lipid peroxidation together with mitochondrial DNA mutation in human lung tissues during aging—Smoking enhances oxidative stress on the aged tissues. Arch. Biochem. Biophys. 362(2): 309-16, 1999.
Liu CS, Kao SH, Wei YH. Smoking-Associated Mitochondrial DNA Mutations in Human Hair Follicles. Environ. Mol. Mutagen 30(1): 47-55, 1997.
Lopez, J.V. et al. (1994) Numt, a recent transfer and tandem amplification of mitochondrial DNA to the nuclear genome of the cat. J. Mol. Evol. 39, 174-190.
Lowes S, Krishnan K, Lindsey J, Lusher M and Brich-Machin MA. British Society for Investigative Dermatology Annual Meeting. British Journal of Dermatology (2002), 146, 736.
Meibner C, Von Wurmb N, Oehmichen M., Detection of the age-dependent 4977 bp deletion of mitochondrial DNA; a pilot study, Int. J. Legal Med. 110: 288-291, 1997.
Michikawa Y, Mazzucchelli F, Bresolin N, Scarlato G, Attardi G., Aging-Dependent Large Accumulation of Point Mutations in the Human mtDNA Control Region for Replication. Science 286: 774-779, 1999.
Miquel J, De Juan E, Sevila I. Oxygen-induced mitochondrial damage and aging. EXS 62:47-57, 1992.
Nachman MW, Brown WM, Stoneking M, Aquardo CF., Nonneutral Mitochondrial DNA Variation in Humans and Chimpanzees. Genetics 142:953-963, 1996.
Naviaux, RK., Mitochondrial Disease—Primary Care Physican's Guide. Psy-Ed. Corp D/B/A Exceptional Parents Guide: 3-10, 1997.
Yu, B, et al.; DNA mutation detection using denaturing high-performance liquid chemoatography (DHPLC). Current protocols in human genetics 19, 7.10.1-14, 1998.
Ozen M, et al, Telomeric DNA Marker for Human Prostate Cancer Development?. Prostate 36:264-271, 1998.
Pang et al, Human Skin Mitochondrial DNA Deletions Associated with Light Exposure. Arch. Biochem. Biophys. 312:(2), 534-538, 1994.
Parsons TJ, et al., A high observed substitution rate in the human mitochondrial DNA control region. Nature Genet. 15 (4):363-368, 1997.
Pascucci B, et al., DNA repair of UV photoproducts and mutagenesis in human mitochondrial DNA. J.Mol.Biol. 273 (2):417-427, 1997.
Penta JS, Johnson FM, Wachsman JT, Copeland, W.C., Mitochondrial DNA in human malignancy, Mut. Res. 488, 119-133, 2001.
Polyak K, et al., Somatic mutations of the mitochondrial genome in human colorectal tumours. Nature Genet. 20 (3):291-293, 1998.
Harman, K.E. et al., Defining Target Antigens in Linear IgA Disease Using Skin From Patients with Inherited Genodermatoses as Substrates For Indirect Immunoflurescence Microscopy; Br. J. of Derm, 138, p. 733 (1998).
Ray AJ, et al. Abstract of the British Society for Investigative Dermatology, Annual Meeting—Cardiff, Apr. 7-9, 1999, Brit.J. Dermatol.140:788, 1999.
Ray AJ, Turner R, Nikaido O, Rees JL, Birch-Machin MA., The spectrum of mitochondrial DNA deletions is a ubiquitous marker of ultraviolet radiation exposure in human skin. J. Invest. Dermatol 115(4):674-679, 2000.

(56) References Cited

OTHER PUBLICATIONS

Rees JL, Skin cancer [Gorlin's Syndrome], In:The Genetic Basis of Human Cancer, eds Vogelstein B, Kinzler K. New York: McGraw-Hill, pp. 527-536, 1998.
Rehman I, Quinn AJ, Healy E, Rees JL. High-frequency of loss of heterozygosity in actinic keratoses, a usually benign disease. Lancet 344: 788-789, 1994.
Rehman I, Takata M, Wu YY, Rees JL. Genetic change in actinic keratoses. Oncogene 12: 2483-2490, 1996.
SAS Enterprise Mining Users Guide, SAS Inc., 2000.
Sawyer E, Van Houten B., Repair of DNA damage in mitochondria. Mutation Res: 434(3):161-176, 1999.
Schurr TG, Ballinger SW, Gan Y, Hodge JA, Merriwether DA, Lawrence DN, Knowler WC, Weiss KM, and Wallace DC., Amerindian Mitochondial DNAs Have Rare Asian Mutations at high Frequencies, Suggesting They Derived from Four Primary Maternal Lineages. Am. J. Hum. Genet. 46:613-623, 1990.
Seidman, M.D. et al., Mitochondrial DNA deletions associated with aging and presbyacusis. Arch. Otolaryngol Head Neck Surg., 123: 1039-1045, 1997.
Shankey TV, Jin JK, Dougherty S, Flanigan RC, Graham S, Pyle JM., DNA-ploidy and proliferation heterogeneity in human prostate cancers. Cytometry 21:30-39, 1995.
Shay JW, Werbin H., Are Mitrochondrial DNA Mutations Involved in the Carcinogenic Process?. Mutat. Res:186: p. 149-160, 1987.
Sherrat EJ, Thomas AW, Alcolado. Mitochondrial DNA defects: A widening clinical spectrum of disorders. JC., Clin. Sci. 92:225-235, 1997.
Shoffner JM, Brown MD, Torroni A, Lott MT, Cabell MF, Mirra SS, Beal MF, Yang C, Gearing M, Salvo R, Watts RL, Juncos JL, Hansen LA, Crain BJ, Fayad M, Reckford CL, and Wallace DC., Mitochondrial DNA Variants Observed in Alzheimer Disease and Parkinson Disease Patients, Genomics 17: 171-184, 1993.
Smith DG, Malhi RS, Eshleman J, Lorenz JG and Kaestle FA., Distribution of mtDNA haplogroup X among Native North Americans. Am. J. Hum. Genet. 110:271-284, 1999.
Smith R, Birch-Machin MA, Rees JL. Melanocortin 1 receptor variants in an Irish population. J. Invest. Dermatol. 111: (1) Jul. 1998, 101-104.
Tamura S, et al. Mutations in mitochondrial control region DNA in gastric tumours of Japanese patients. Eur.J.Cancer [A] 35 (2):316-319, 1999.
Tanaka, M. et al, 1996, Automated sequencing of mtDNA, Methods Enzymol. 264: 407-421.
Taniike, M. et al., Mitochondrial transfer rnaile mutation in fatal cardiomyopathy. BioChem BioPhys Res Comun, 186: 47-53, 1992.
Taylor RW, Birch-Machin MA, Bartlett K, Turnbull DM., The control of mitoch. oxidations by complex-III in rat muscle and liver-mitochondria—implications for our understanding of mitochondrial cytopathies in man. J Biol Chem, 269, 3523-3528 1994.
Torii K. et al., Aging-associated deletions of human diaphragmatic mitochondrial DNA, Am. J. Respir. Cel.l Mol. Biol. In press 1992, p. 543-549.
Valnot, Isabelle, et al., A mitochondrial cytochrome b mutation but no mutations of nuclearly encoded subunits in ubiquinol cytochrome c reductase (complex III) deficiency, Human Genetics (1999) 104: 460-466.
Van Den Bosch BJC, et al., Mutation analysis of the entire mitochondrial genome using denaturing high performance liquid chromatography. Nucleic Acids Res. 28: 89, 2000.
Von Wurmb, N, Oehmichen, M, Meissner, C., Demonstration of the 4977 bp deletion in human mitochondrial DNA from intravital and postmortem blood. Mutat Res. 422:247-254, 1998.
Wallace DC., Diseases of the mitochondrial-DNA. Annu Rev Biochem, 61: 1176-1212, 1992.
Wallace DC. Mitochondrial-DNA sequence variation in human-evolution and disease. Proc. Natl. Acad. Sci. USA 91: 8739-8746, 1994.
Wallace, D.C., Mitochondrial Diseases in man and Mouse. Science, 5(283): 1482-1497, 1999.

Wallace et al., Mitochondiral DNA Mutation Associated with Leber's Hereditary Optic Neuropathy, Science, 1427-1429; 1988.
Walsh PC, Partin, AW, Family history facilitates the early diagnosis of prostate carcinoma. Cancer 80:Nov. 1, 1997, vol. 80, No. 9; pp. 1871-1874.
Ward RH, Frazier BL, Dew-Jager K, Paabo S., Extensive mitochondrial diversity within a single amerindian tribe. Proc. Natl. Acad. Sci. USA 88:8720-8724, 1991.
Wei YH, Pang C, You B, Lee H., Tandem Duplications and Large-Scale Deletions of Mitochondrial DNA Are Early Molecular Events of Human Aging Process, Annals NY Acad. of Sciences 786:82-101, 1996.
Wei YH. Mitochondrial DNA Mutations and Oxidative Damage in Aging and Diseases: An Emerging Paradigm of Gerontology and Medicine; Proc. of the Nat. Sci. Council of the ROC, vol. 22(2):1998, pp. 55-67 1997.
Weinstock MA: Epidemiology of ultraviolet radiation. In: JJ Stern RS, MacKie RM and Weinstock MA, Grob (eds) Epidemiology, Blackwell (UK). pp. 121-128, 1998.
Wu & Wallace., The ligation amplification reaction (LAR)—amplification of specific DNA-sequences using sequential rounds of template-dependent ligation. Genomics, 4:560, 1989.
Xu J, et al., Evidence for a prostate cancer susceptibility locus on the X chromosome. Nature Genet 20: 175-179,1998.
Yamaguchi KT, et al., Measurement of free-radicals from smoke-inhalation and oxygen exposure by spin trapping and esr spectroscopy. Free Radical Res. Commun. 16(3):167-74, 1992.
Yeh, J.J., et al., Somatic mitochondrial DNA (mtDNA) mutations in papillary thyroid carcinomas and differential mtDNA sequence variants in cases with thyroid tumours. Oncogene Journal, 19: 2060-2066, 2000.
Yen et al., Ageing-associated 5kb deletion in human liver mitochondrial DNA, Biochem., Biophys., Res. Commun., 178, 124-131 1991.
Yen et al., Age-dependent 6 kb deletion in human liver mitochondrial DNA, Biochem. Int. 26, 457-468 1992.
Zeviani M, et al. Nucleus-driven Multiple Large-Scale Deletions of the Human Mitochondrial Genome: A New Autosomal Dominant Disease. Am. J. Hum. Genet. 47:904-914, 1990.
Zhang et al., Multiple mitochondiral DNA deletions in an elderly human individual, FEBS Lett, 297, 34-38 1992.
Zhang, C., et al., Occurrence of a Particular Base Substitution (3243 a to G) in Mitochondrial DNA of Tissues of Ageing Humans. BioChem. BioPhys. Res. Comun., 195: 1104-1110, 1993.
Jessie B et al., "Accumulation of mitochondrial DNA deletions in the aging prostate." Proceedings of the American Association for Cancer Research Annual, vol. 42, Mar. 2001, pp. 862-863, XP001153110. 92nd Annual Meeting of the American Association for Cancer Research; New Orleans, LA, USA; Mar. 24-28, 2001. ISSN: 0197-016X.
Thayer R et al., "Mitochondrial DNA mutations and/or deletions in prostate cancers," Proceedings of the American Association for Cancer Research Annual, vol. 42, Mar. 2001, pp. 532-533, XP001153105. 92nd Annual Meeting of the American Association for Cancer Research, New Orleans, LA, USA; Mar. 24-28, 2001. ISSN: 0197-016X.
Petros JA. et al., "Mitochondrial DNA point mutations are common in prostate cancer and enhance malignant phenotype," Proceedings of the American Association for Cancer Research Annual, vol. 42, Mar. 2001, p. 517, XP001153111. 92nd Annual Meeting of the American Association for Cancer Research, New Orleans, LA, USA; Mar. 24-28, 2001. ISSN: 0197-016X.
Jeronimo C. et al., "Mitochondrial mutations in early stage prostate cancer and bodily fluids," Proceedings of the American Association for Cancer Research Annual, vol. 42, Mar. 2001, p. 63, XP001153112. 92nd Annual Meeting of the American Association for Cancer Research, New Orleans, LA, USA; Mar. 24-28, 2001. ISSN: 0197-016X.
Eshaghian A. et al., "Alterations of mitochondrial DNA in aging skin and in non-melanoma skin cancers," Proceedings of the American Association for Cancer Research Annual, vol. 43, Mar. 2002, pp. 304-305, XP001153120, 93rd Annual Meeting of the American Association for Cancer Research, San Francisco, California, USA, Apr. 6-10, 2002, ISSN: 0197-016X.

(56) References Cited

OTHER PUBLICATIONS

Hardy et al. Ethnic Differences and Disease Phenotypes. Science 2003 vol. 300, p. 737-781.
Hirschorn et al. A comprehensive review of genetic association studies. 2002 Genetics in Medicine p. 45-61.
Lucentini, J., Gene association studies typically wrong, reproducible gene-disease associations are few and far between, The Scientist, Dec. 20, 2004, p. 20.
Ioannidis J. et al, Replication validity of genetic association studies. Nature Genetics 2001 vol. 29 p. 306-309.
Buzzi et al. mtDNA A3243G MELAS mutation is not associated with multigenerational female migraine. Neurology 2000 vol. 54 p. 1005-1007 Abstract.
Kogelnik Andreas M et al., "MITOMAP: A human mitochondrial genome database—1998 update," Nucleic Acids Research, Oxford University Press, Surry, GB, vol. 26, No. 1, 1998, pp. 112-115, XP002966479, ISSN: 0305-1048.
Bandelt Hans-Jurgen et al., "What is 'novel' mtDNA mutation—and does 'novelty' really matter?" Journal of Human Genetics 2006, vol. 51, No. 12, 2006, pp. 1073-1082, XP002450142, ISSN: 1434-5161.
Croation Medical Journal, vol. 42, No. 3, 2001, Thomas J. Parsons et al., "Increasing the forensic discrimination of mitochondrial DNA testing through analysis of the entire mitochondrial DNA genomes", pp. 304-309.
Nature, vol. 408, Dec. 2000, Max Ingman et al., "Mitochondrial genome variation and the origin of modern humans," pp. 708-713.
Genomics, vol. 55, 1999, Barbara C. Levin et al., "A human mitochondrial DNA standard reference material for quality control in forensic identification, medical diagnosis, and mutation detection," pp. 135-146.
Biotechniques, vol. 32, No. 1, Jan. 2002, H. Andreasson et al: "Mitochondrial Sequence Analysis for Forensic Identification Using Pyrosequencing Technology," pp. 124-133.
Harbottle et al., Implications of Using the ND1 Gene as a Control Region for Real-Time PCR Analysis of Mitochondrial DNA Deletions in Human Skin. The Journal of Investigative Dermatology: 1518-1521, 2004.
Maitra, A. et al. The Human MitoChip: A High-Throughput Sequencing Microarray for Mitochondrial Mutation Detection. Genome Res. May 2004, vol. 14, No. 5, pp. 812-819 (plus cover page), ISSN 1088-9051.
Krishnan, K.J. et al. The Use of a 3895 bp Mitochondrial DNA Deletion as a Marker for Sunlight Exposure in Human Skin. J. Invest. Dermatol. Dec. 2004, vol. 123, No. 6, pp. 1020-1024. ISSN 0022-202X.
Prithivirajsingh, S. et al. Accumulation of Common Mitochondrial DNA Deletion Induced by Ionizing Radiation. FEBS Lett. Aug. 2004, vol. 571, pp. 227-232. ISSN 0014-5793.
Chabi, B. et al., Quantification of Mitochondrial DNA Deletion, Depletion,and Overreplication: Application to Diagnosis. Clin. Chem. Aug. 2003, vol. 49, No. 8, pp. 1309-1317. ISSN 0009-9147.
Mutation Research, 2000, vol. 468, pp. 35-43. CC to TT mutation in the mitochondrial DNA of normal skin: relationship to ultraviolet exposure, Kawasaki et al.
Nucleic Acids Res., Denaturing high performance liquid chromatography (DHPLC) used in the detection of germline and somatic mutations. vol. 26, No. 6, pp. 1396-1400, 1998, Lin et al.
Parrella P. et al., Detection of Mitochondrial DNA Mutations in Primary Breast Cancer and Fine-Needle Aspirates, Cancer Research, 61, 7623-7626, 2001.
Chen, J. et al., Extensive Somatic Mitochondrial Mutations in Primary Prostate Cancer Using Laser Capture Microdissection, Cancer Research, 62, 6470-6474, 2002.
Fliss, M. et al., Facile Detection of Mitochondrial DNA Mutations in Tumors and Bodily Fluids, Science, 287, 2017-2019, 2000.
Jeronimo, C. et al., Mitochondrial mutations in early stage prostrate cancer and bodily fluids, Oncogene, 20, 5195-5198, 2001.
Chen, J. et al., Simultaneous generation of multiple mitochondrial DNA mutations in human prostrate tumors suggests mitochondrial hyper-mutagenesis, Carcinogenesis, vol. 24, No. 9, pp. 1481-1487, 2003.
Bugart, L. et al., Somatic Mitochondrial Mutation in Gastric Cancer, American Journal of Pathology, 147, 1105-1111, 1995.
Jessie, B. et al., Accumulation of mitochondrial DNA deletions in the malignant prostate of patients of different ages, Experimental Gerontology 37, 169-174, 2001.
Zhu, Weizhu, M.D. et al., Large-scale mitochondrial DNA deletion mutations and nuclear genome instability in human breast cancer. Cancer Detection and Prevention, 28, pp. 119-126 copyrighted 2004 International Society for Preventative Oncology.
He, L. et al.:"Detection and quantification of mitochondrial DNA deletions in individual cells by real-time PCR." Nucleic Acids Research [online], Jul. 15, 2002 (Jul. 15, 2002) {retrieved on Apr. 3, 2008], vol. 30, No. 14, p. 68, ISSN:1362-4962. Retrieved from Internet: <URL: http://nar.oxfordjournals.org/cgi/reprint/30/14e68>.
Maki, J. et al.; "Mitrochondrial genome deletion aids in the identification of false-and true-negative prostate needle core biopsy specimens," American Journal of Clinical Pathology, Jan. 2008, vol. 129, No. 1, pp. 57-66, ISSN: 0002-9173.
Huoponen, Kirsi, Leber hereditary optic neuropathy: clinical and molecular genetic findings, Neurogentics (2001) 3: 119-125.
Huang GM, NG WL, Farkas J, He L, Liang HA, Gordon D, Hood R., Genomics 59(2): 178-86, 1999.
Landis SH, Murray T, Volden S, Wingo PA. Cancer J. Clin 49:8-31.
Kogelnik et al, Nuel. Acids Res. 26(1), 112 (1998) MITOMAP: A human mt genome database (www.gen.emory.edu/mitomap.html).
Wei YH., Proceedings of the Nat Sci. Council of the Republic of China. Apr. 22(2):5567, 1998.
Woowell DA., National Ambulatory Medical Care Survey: 1997 Summary. Advance data from vital and health statistics; No. 305. Hyattsville, Maryland: National Center for Health Statistics. 1999.

\* cited by examiner

3.4 KB MITOCHONDRIAL DNA DELETION FOR USE IN THE DETECTION OF CANCER

CROSS REFERENCE TO RELATED APPLICATIONS

This application is a continuation of U.S. patent application Ser. No. 14/874,155, filed Oct. 2, 2015, which is a continuation of U.S. patent application Ser. No. 14/507,027, filed Oct. 6, 2014, which is a continuation of U.S. patent application Ser. No. 12/748,120, filed Mar. 26, 2010, which is a continuation-in-part of U.S. patent application Ser. No. 11/975,390, filed Oct. 18, 2007, now U.S. Pat. No. 8,008,008 issued Aug. 30, 2011, which is a continuation of PCT/CA2006/000652, filed Apr. 18, 2006, which PCT application claims the benefit under 35 U.S.C. § 119(e) of U.S. Provisional Patent Application Nos. 60/672,016, filed Apr. 18, 2005; 60/721,522, filed Sep. 29, 2005; and 60/789,872, filed Apr. 7, 2006, which applications are hereby incorporated by reference in their entireties. Additionally, this application is a continuation of U.S. patent application Ser. No. 14/874,155, filed Oct. 2, 2015, which is a continuation of U.S. patent application Ser. No. 14/507,027 filed Oct. 6, 2014 which is a continuation of U.S. patent application Ser. No. 12/748,120, filed Mar. 26, 2010, which is a continuation of PCT/CA2007/001711, filed Sep. 26, 2007, which applications are hereby incorporated by reference in their entireties.

REFERENCE TO SEQUENCE IDENTIFICATION LISTING

The present application includes a sequence identification listing in .txt format as follows:
Filename: Sequence Listing re PCT International Patent Appl. No. PCT_CA2007_001711.txt
Size: 26.8 KB
Date Created: Mar. 22, 2010
This sequence identification listing is hereby expressly incorporated by reference in its entirety in the present application.

FIELD OF THE INVENTION

This invention is related to the field of mitochondrial genomics. In particular it is related to a 3.4 kb deletion in the mitochondrial genome and its utility as an indicator of cancer.

BACKGROUND OF THE INVENTION

Mitochondrial DNA (MtDNA) as a Diagnostic Tool

MtDNA sequence dynamics are important diagnostic tools. Mutations in mtDNA are often preliminary indicators of developing disease, often associated with nuclear mutations, and act as biomarkers specifically related to: disease, such as but not limited to, tissue damage and cancer from smoking and exposure to second hand tobacco smoke (Lee et al., 1998; Wei, 1998); longevity, based on accumulation of mitochondrial genome mutations beginning around 20 years of age and increasing thereafter (von Wurmb, 1998); metastatic disease caused by mutation or exposure to carcinogens, mutagens, ultraviolet radiation (Birch-Machin, 2000); osteoarthritis; cardiovascular, Alzheimer, Parkinson disease (Shoffner et al., 1993; Sherratt et al., 1997; Zhang et al, 1998); age associated hearing loss (Seidman et al., 1997); optic nerve degeneration and cardiac dysrhythmia (Brown et al., 1997; Wallace et al., 1988); chronic progressive external exophthalmoplegia (Taniike et al., 1992); atherosclerosis (Bogliolo et al., 1999); papillary thyroid carcinomas and thyroid tumours (Yeh et al., 2000); as well as others (e.g. Naviaux, 1997; Chinnery and Turnbull, 1999).

Mutations at specific sites of the mitochondrial genome can be associated with certain diseases. For example, mutations at positions 4216, 4217 and 4917 are associated with Leber's Hereditary Optic Neuropathy (LHON) (Mitochondrial Research Society; Huoponen (2001); MitoMap). A mutation at 15452 was found in 5/5 patients to be associated with ubiquinol cytochrome c reductase (complex III) deficiency (Valnot et al. 1999).

Specifically, these mutations or alterations include point mutations (transitions, transversions), deletions (one base to thousands of bases), inversions, duplications, (one base to thousands of bases), recombinations and insertions (one base to thousands of bases). In addition, specific base pair alterations, deletions, or combinations thereof have been found to be associated with early onset of prostate, skin, and lung cancer, as well as aging (e.g. Polyak et al., 1998), premature aging, exposure to carcinogens (Lee et al., 1998), etc.

Prostate Cancer

Prostate cancer is a frequently diagnosed solid tumour that most likely originates in the prostate epithelium (Huang et al. 1999). In 1997, nearly 10 million American men were screened for prostate specific antigen (PSA), the presence of which suggests prostate cancer (Woodwell, 1999). Indeed, this indicates an even higher number of men screened by an initial digital rectal exam (DRE). In the same year, 31 million men had a DRE (Woodwell, 1999). Moreover, the annual number of newly diagnosed cases of prostate cancer in the United States is estimated at 179,000 (Landis et al., 1999). It is the second most commonly diagnosed cancer and second leading cause of cancer mortality in Canadian men. In 1997 prostate cancer accounted for 19,800 of newly diagnosed cancers in Canadian men (28%) (National Cancer Institute of Canada). It is estimated that 30% to 40% of all men over the age of forty-nine (49) have some cancerous prostate cells, yet only 20% to 25% of these men have a clinically significant form of prostate cancer (SpringNet—CE Connection, internet, www.springnet.com/ce/j803a.htm). Prostate cancer exhibits a wide variety of histological behaviour involving both endogenous and exogenous factors, i.e. socio-economic situations, diet, geography, hormonal imbalance, family history and genetic constitution (Konishi et al. 1997; Hayward et al. 1998). Although certain mtDNA alterations have been previously associated with prostate cancer, the need exists for further markers for the detection of prostate cancer.

3.4 kb mtDNA Deletion and the Detection of Prostate Cancer.

In the applicant's pending PCT application bearing publication no. WO/06/111029 (the entire contents of which are incorporated herein by reference) a deletion of a 3379 bp segment of mtDNA was identified through full mitochondrial genome amplification of prostate tissue. The 3379 bp deletion (referred to as the 3.4 kb deletion) was determined to be spanning nucleotides 10744-14124 of the mitochondrial genome. It was determined that the detection of this deletion could be used in the diagnosis of prostrate cancer when tissue samples are tested.

The 3.4 kb deletion removes all or part of the following genes from the mtDNA genome: (i) NADH dehydrogenase subunit 4L, (ii) NADH dehydrogenase subunit 4, (iii)

NADH dehydrogenase subunit 5, (iv) tRNA histidine, (v) tRNA serine2, and (vi) tRNA leucine2.

Breast Cancer

Breast cancer is a cancer of the glandular breast tissue and is the fifth most common cause of cancer death. In 2005, breast cancer caused 502,000 deaths (7% of cancer deaths; almost 1% of all deaths) worldwide (World Health Organization Cancer Fact Sheet No. 297). Among women worldwide, breast cancer is the most common cancer and the most common cause of cancer death (World Health Organization Cancer Fact Sheet No. 297). Although certain mtDNA alterations have been previously associated with breast cancer, for example, in Parrella et al. (Cancer Research: 61, 2001), the need exists for further markers for the detection of breast cancer.

BRIEF SUMMARY OF THE INVENTION

In one embodiment, the present invention provides a method of detecting a cancer in an individual comprising;
a) obtaining a biological sample from the individual;
b) extracting mitochondrial DNA, mtDNA, from the sample;
c) quantifying the amount of mtDNA in the sample having a deletion in the nucleic acid sequence spanning approximately residues 10744 and 14124 of the mtDNA genome;
d) comparing the amount of mtDNA in the sample having the deletion to at least one known reference value.

In one embodiment, the present invention provides a method of detecting a cancer in an individual comprising;
a) obtaining a biological sample from the individual;
b) extracting mitochondrial DNA, mtDNA, from the sample;
c) quantifying the amount of mtDNA in the sample having a deletion in the nucleic acid sequence spanning approximately residues 10744 and 14124 of the mtDNA genome;
d) comparing the amount of mtDNA in the sample having the deletion to the amount of the deletion in a reference sample of mtDNA from known non-cancerous tissue or body fluid;
wherein an elevated amount of the deletion in the biological sample compared to the reference sample is indicative of cancer.

In one embodiment, the present invention provides a method of detecting a cancer in an individual comprising;
a) obtaining a biological sample from the individual;
b) extracting mitochondrial DNA, mtDNA, from the sample;
c) quantifying the amount of mtDNA in the sample having a deletion in the nucleic acid sequence spanning approximately residues 10744 and 14124 of the mtDNA genome;
d) comparing the amount of mtDNA in the sample having the deletion to the amount of the deletion in a reference sample of mtDNA from known cancerous tissue or body fluid;
wherein a similar level of the deletion in the biological sample compared to the reference sample is indicative of cancer.

In one embodiment, the present invention provides a method of monitoring an individual for the development of a cancer comprising;
a) obtaining a biological sample;
b) extracting mtDNA from the sample;
c) quantifying the amount of mtDNA in the sample having a deletion in the nucleic acid sequence spanning approximately residues 10744 and 14124 of the mtDNA genome;
d) repeating steps a) to c) over a duration of time;
e) wherein an increasing level of the deletion over the duration of time is indicative of cancer.

In one embodiment, the present invention provides a method of detecting a cancer in an individual comprising;
a) obtaining a biological sample from the individual;
b) extracting mitochondrial DNA, mtDNA, from the sample;
c) quantifying the amount of mtDNA in the sample having a sequence corresponding to the sequence identified in SEQ ID NO: 1;
d) comparing the amount of mtDNA in the sample corresponding to SEQ ID NO: 1 to at least one known reference value.

BRIEF DESCRIPTION OF THE SEVERAL VIEWS OF THE DRAWINGS

An embodiment of the invention will now be described by way of example only with reference to the appended drawings wherein.

DETAILED DESCRIPTION OF THE INVENTION

Figure 1:
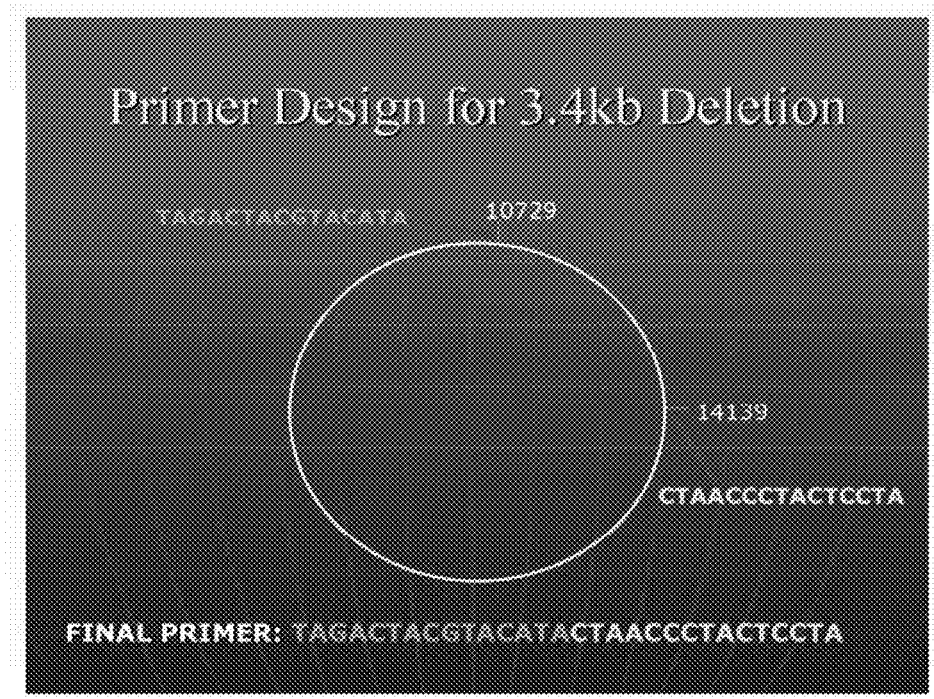
FIG. 1 is a schematic diagram showing the design and sequence of a primer useful for the detection of the 3.4 kb deletion. The primer (SEQ ID NO: 2) binds to bases 10729-10743/14125-14139 of the mtDNA genome, wherein the portion of the primer that binds to bases 10729-10743 is depicted in gray in the upper left corner of the figure (nucleotides 1-15 of SEQ ID NO: 2) and the portion of the primer that binds to bases 14125-14139 is depicted in white in the lower right corner of the figure (nucleotides 16-30 of SEQ ID NO: 2)

As used herein, "cycle threshold" ($C_T$) is the point at which target amplification using real-time PCR rises above background, as indicated by a signal such as a fluorescence signal. The $C_T$ is inversely related to the quantity of the sequence being investigated.

As defined herein, "sensitivity" refers to the fraction of true positives (true positive rate) results obtained using the method of the present invention.

As defined herein, "specificity" refers to the fraction of false positives (false positive rate) results obtained using the method of the present invention.

In one embodiment of the present invention, methods are provided for monitoring and diagnosing cancer through the detection and quantification of the aforementioned 3.4 kb mtDNA deletion. For example, the present invention may be used for detecting the presence of pre-neoplasia, neoplasia and progression towards potential malignancy of prostate cancer and breast cancer. In one aspect, the present invention involves the detection and quantification of the 3.4 kb mtDNA deletion (SEQ ID NO:1) for the detection, diagnosis, and/or monitoring of cancer. In this method, mtDNA is extracted from a biological sample (for example body tissue, or body fluids such as urine, prostate massage fluid). The extracted mtDNA is then tested in order to determine the levels (i.e. quantity) of the 3.4 kb deletion in the sample. In tests conducted by the present inventors, the levels of the deletion were found to be elevated in samples obtained from subjects with cancer when compared to samples obtained from subjects without cancer. Based on the information and data supplied below, the inventors have concluded that elevated levels of the 3.4 kb deletion in the mtDNA is indicative of cancer.

As disclosed in PCT WO/06/111029, the 3.4 kb deletion spans approximately nucleotides 10744 to 14124 of the mtDNA genome. The mtDNA genome is listed as SEQ ID NO:8 (Genbank accession no. AC 000021). The inventors have determined, as provided by example below, that this deletion is also associated with cancer and in particular prostate and breast cancer. Therefore, such deletion provides an accurate biomarker and, therefore, a valuable tool for the detection, diagnosis, or monitoring of cancer in at least these tissues.

The deletion results in the creation of two deletion monomers, one of 3.4 kb in size (small sublimon) and one of approximately 12.6 kb in size (large sublimon). The occurrence of the deletion may be detected by either identifying the presence of the small sublimon, or by determining that the 3.4 kb sequence has been deleted from the large sublimon.

As discussed above, the deletion is approximately 3379 bp, and comprises genes encoding NADH dehydrogenase subunit 4L, NADH dehydrogenase subunit 4, NADH dehydrogenase subunit 5, tRNA histidine, tRNAserine2, and tRNA leucine2.

In one embodiment, samples of, for example prostate tissue, prostate massage fluid, urine or breast tissue, are obtained from an individual and tested over a period of time (e.g. years) in order to monitor the genesis or progression of cancer. Increasing levels of the 3.4 kb deletion over time could be indicative of the beginning or progression of cancer.

Age related accumulation of the 3.4 kb mtDNA deletion may predispose an individual to, for example, prostate cancer or breast cancer, which is prevalent in middle aged and older men, and middle aged and older women, respectively. According to one aspect of the invention, a method is provided wherein regular cancer screening may take place by monitoring over time the amount of the 3.4 kb deletion in body tissues such as breast tissue or body fluids such as prostate massage fluid, or urine.

The system and method of the present invention may be used to detect cancer at an early stage, and before any histological abnormalities. For example, the system and method of the present invention may be used to detect pre-neoplasia in breast tissue.

The following primer sequences are preferred for the detection of the 3.4 kb deletion:

```
3.4 forward (binds to bases 10729-10743/14125-
14139 of the mtDNA genome)
                                   (SEQ ID NO: 2)
5'-TAGACTACGTACATACTAACCCTACTCCTA-3';
```

```
3.4 reverse (binds to bases 14361-14379 of the
mtDNA genome)
                                   (SEQ ID NO: 3)
5'-GAGGTAGGATTGGTGCTGT-3'.
```

In one embodiment of the present invention, a pair of amplification primers are used to amplify a target region indicative of the presence of the 3.4 kb deletion. In this embodiment, one of the pair of amplification primers overlaps a spliced region of mtDNA after deletion of the 3.4 kb sequence has occurred (i.e. a splice at a position spanning approximately residues 10744 and 14124 of the mtDNA genome). Therefore, extension of the overlapping primer can only occur if the 3.4 kb section is deleted.

In another embodiment of the present invention, a pair of amplification primers are used to amplify a target region associated with the deleted 3.4 kb sequence. The deleted 3.4 kb sequence, upon deletion, may reform as a circular mtDNA molecule. In this embodiment, one of the pair of amplification primers overlaps the rejoining site of the ends of the 3.4 kb sequence. Thus, an increase in the amount of the 3.4 kb molecule detected in a sample is indicative of cancer. The below primer pair is preferred for the detection of the deleted 3.4 kb nucleic acid.

```
Forward 14115/10755
                                   (SEQ ID NO: 9)
5'-CCCACTCATCACCTAAACCTAC-3'

Reverse 10980R
                                   (SEQ ID NO: 10)
5'-GGTAGGAGTCAGGTAGTTAG-3'.
```

In one aspect of the invention, a kit for diagnosing cancer, for example prostate or breast cancer, comprising means for extraction of mtDNA, primers having the nucleic acid sequences recited in SEQ ID NOS: 2 and 3, or SEQ ID NOS: 9 and 10, reagents and instructions, is provided.

Another aspect of the invention provides methods for confirming or refuting the presence of a cancer biopsy test from a biopsy sample (e.g. prostate or breast cancer), comprising: obtaining non-cancerous tissue from a biopsy sample; and detecting and quantifying the amount of the 3.4 kb mtDNA deletion in the non-diseased tissue.

In one embodiment the present invention provides a method for screening individuals for prostate or breast cancer from a body fluid sample comprising; obtaining a body fluid sample, and detecting and quantifying the level of the 3.4 kb mtDNA deletion in the body fluid.

Although real-time quantitative PCR methods, as described in the examples below, represent the preferred means for detecting and quantifying the presence or absence of the 3.4 kb deletion, other methods that would be well known to an individual of skill in the art could also be utilized. For example quantification of the deletion could be made using Bio-Rad's Bioplex™ System and Suspension Array technology. Generally, the method requires amplification and quantification of sequences using any known methods.

The examples provided below illustrate that not only can this deletion be used for the detection of prostate cancer in prostate tissue, but can also be used to detect the presence of cancer in other biological samples, for example prostate massage fluid, urine, and breast tissue. Based on the findings in these examples, the 3.4 kb mtDNA deletion may be used as a biomarker for cancer.

The various examples provided illustrate a difference in the amount of mtDNA having the 3.4 kb deletion between samples obtained from subjects having cancer, and subjects without cancer. The amount of the 3.4 kb deletion was found to be higher in the samples obtained from subjects having cancer. This determination was made by comparing the amount of the 3.4 kb deletion in the test samples with amounts from known cancer cells and/or known non-cancer cells.

Example 1: 3.4 kb Deletion in the mtDNA of Prostate Tissue

A deletion of approximately 3.4 kilobases (kb) was identified through full mitochondrial genome amplification of fresh frozen prostate tissue. Using linear regression, the size of the deletion was estimated to be between 3000 base pairs (bp) and 3500 bp. Two possible candidate deletions were identified using Mitomap™ (Brandon, M. C., Lott, M. T., Nguyen, K. C., Spolim, S., Navathe, S. B., Baldi, P. & Wallace, D. C., MITOMAP: a human mitochondrial genome database—2004 update. Nucleic Acids Research 33 (Database Issue):D611-613, 2005; www.mitomap.org), the 3397 bp deletion at 9574-12972, and the 3379 bp deletion at 10744-14124. In order to determine which of the two deletions was associated with prostate cancer, if either, a forward primer which bridged the deletion junction was developed for each of the two candidates, ensuring that the primer extended further than the repeat regions that flank the deletions. FIG. 1 is a schematic diagram showing the design and sequence of the primer (i.e. SEQ ID NO: 2). Positive amplification results for the amplicon corresponding to the 3379 bp deletion (referred to as the 3.4 kb deletion) at 10744-14124 were obtained.

As indicated above, the 3.4 kb deletion removes all or part of the following genes: (i) NADH dehydrogenase subunit 4L, (ii) NADH dehydrogenase subunit 4, (iii) NADH dehydrogenase subunit 5, (iv) tRNA histidine, (v) tRNA serine2, and (vi) tRNA leucine2.

The 3.4 kb deletion was determined to be present in 91% of 33 fresh frozen prostate samples. With the specific deletion primers, formalin fixed tissues were tested in order increase the n value.

The present investigators sequenced entire mitochondrial genomes from 32 tissue samples microdissected by laser capture microdisection and 12 needle biopsies from histologically normal prostates. Archived tissue sections from each of these samples were used for the following study. 1-2 serial sections were removed from each sample. DNA was extracted from each sample in its entirety rather than as a microdissection. Thus, each sample consisted of a mixture of glandular prostate tissue as well as stromal prostate tissue. This extraction was performed using Qiagen's QIAamp™ DNA Mini Kit (Cat #51304). Following extraction the samples were quantified using a Nano-Drop™ spectrophotometer and the concentrations were subsequently normalized to 2 ng/ul. Each sample was amplified using 20 ng input DNA and an iQ SYBR Green Supermix™ kit (Bio-Rad Laboratories Inc.) Reactions were run on an Opticon® 2 two colour real-time PCR system (MJ Research).

Figure 2:
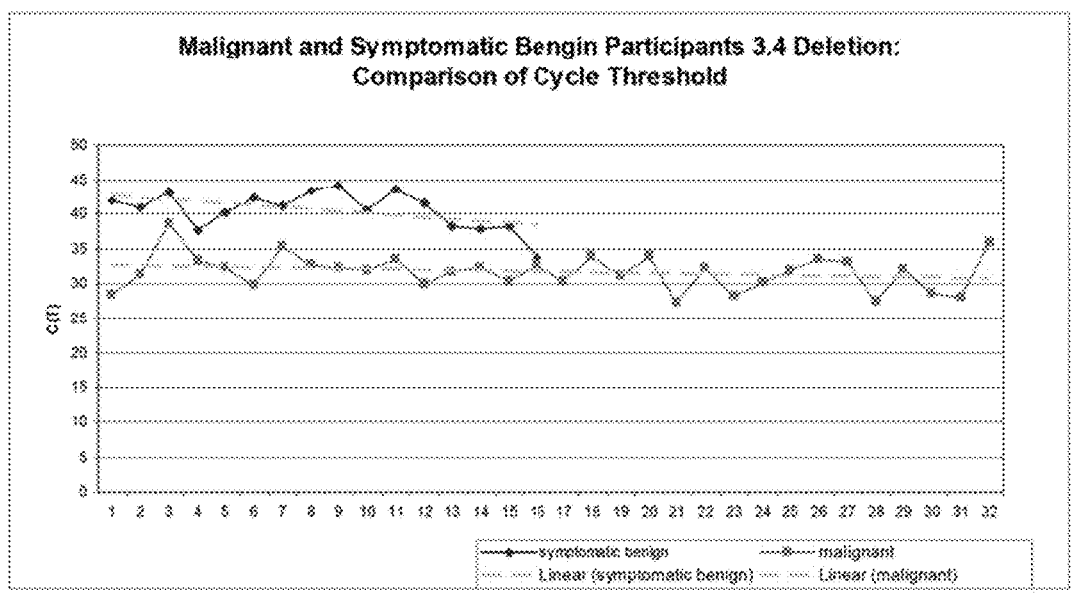
FIG. 2 is a graph showing a comparison of cycle threshold between malignant and symptomatic benign participants in the 3.4 kb study.

As shown in FIG. 2, a distinct difference was observed in cycle threshold and, by extension, quantity of the deletion between the malignant prostate samples and the symptomatic benign prostate samples. Malignant samples exhibited a consistently earlier cycle threshold than the benign samples.

Example 2: 3.4 kb Deletion Blinded Study—Comparison of Cycle Threshold

An additional 21 prostate tissue samples were selected, 10 of which were benign and 11 of which were malignant. The pathological status was determined by needle biopsies conducted by a qualified pathologist. The samples were blinded such that the present investigators were unaware of their pathological status when they conducted this test. The present investigators were able to predict pathological status correctly in 81% of the cases by examining the cycle threshold. Of the 4 incorrect calls, two were malignant samples that were determined to be benign and 2 were benign samples that were determined to be malignant. Follow-up clinical information for the 2 individuals in the latter scenario was requested from the physician to determine if they had been diagnosed with prostate cancer subsequent to the needle biopsy results used for this study. One of the individuals who originally produced a benign sample but was predicted by this study to have a malignancy subsequently produced a malignant sample. As a result, one of the false positives became a true positive. Therefore, pathological status was predicted correctly in 86% of the cases examined in this study. The ultimate positive predictive value (PPV, where PPV=true positives/(true positives+false positives)) for this study was 91% and the negative predictive value (NPV, where NPV=true negatives/(true negatives+false negatives)) was 80%.

Example 3: 3.4 kb Deletion Study—Methods (n=76)

Seventy-six prostate tissue samples were examined for the 3.4 kb deletion in this study. All tissue samples were formalin-fixed, 25 being malignant, 12 being normal, and 39 having benign prostatic disease as shown histologically. Of the latter group more then half had hyperplasia. All specimens were needle biopsies taken from the investigators' tissue archives.

Prostate Specimens

A tapelift was performed on each slide using Prep-Strips (Catalogue Number LCM0207) from Arcturus Bioscience Inc. This allowed the removal of any particulate matter or non-adhering tissue from the slide prior to DNA extraction. With the tissue still on the slides, the slides were rinsed with PBS (Phosphate Buffered Saline Solution) to remove as much fixative as possible. The 1-2 needle biopsy sections on the slides were scraped into sterile microcentrifuge tubes using individually wrapped, sterilized surgical razor blades. DNA was then isolated and purified using a QIAamp® DNA Mini Kit (Qiagen, Cat. #51304) according to manufacturer's specifications. A negative extract control was processed in parallel with the slide extractions as a quality control checkpoint. The total concentration of DNA and purity ratio for each sample was determined by spectrophotometry (Nano-Drop™ ND-1000) and dilutions of 2 ng/µl were prepared for the purpose of Quantitative Polymerase Chain Reaction (qPCR).

Primers (Oligonucleotides)

Purified oligonucleotide primers were chemically synthesized by Invitrogen (California, USA). The sequences of the primers and the expected sizes of the PCR products amplified are listed in Table 1. In addition, PCR analysis for mtDNA deletions included positive controls (DNA from a source known to carry the mutant mtDNA). Each primer set with the exception of TNF (tumor necrosis factor) were checked against a mitochondria-free rho 0 cell line to confirm the absence of pseudogene coamplification.

TABLE 1

Amplification Primers.

| Primer Pair | Position Amplified 5'- 3' | Length of amplified product (base pairs) |
|---|---|---|
| 3.4 Deletion Real-Time | 10729-14379 (less 3379 bp at 10744-14124) | 273 |
| 12s mtDNA | 708-945 | 238 |
| TNF | 3756-3886 | 131 |

3.4 forward (10729-10743 - 14125-14139)
5' TAGACTACGTACATACTAACCCTACTCCTA-3' SEQ ID NO: 2
3.4 reverse (14361-14379) 5'-GAGGTAGGATTGGTGCTGT-3' SEQ ID NO: 3
12s forward (708-728) 5'-CGTTCCAGTGAGTTCACCCTC-3" SEQ ID NO: 4
12s reverse (923-945) 5'-CACTCTTTACGCCGGCTTCTATT-3' SEQ ID NO: 5
TNF forward (3756-3775) 5'-CCTGCCCCAATCCCTTTATT-3' SEQ ID NO: 6
TNF reverse (3866-3886) 5'-GGTTTCGAAGTGGTGGTCTTG-3'SEQ ID NO: 7

Real-Time Polymerase Chain Reaction

Three separate PCRs were performed on each sample. Each reaction was 25 µl total volume and included template DNA, one pair of primers (12s or 3.4 Deletion or TNF), an iQ SYBR Green Supermix™ kit (Catalogue Number 170-8882, Bio-Rad Laboratories Inc.) and distilled deionized water (ddH$_2$O). The TNF (tumor necrosis factor) comprised single copy nuclear gene primers, and 12s comprised total mitochondrial genome primers. The volume and concentrations for template DNA, primers, and reaction buffer are listed below.

TABLE 2 qPCR Components.

| Reagent | Concentration per Reaction | Volume per Reaction |
|---|---|---|
| Reaction Buffer | 1X | 12.5 µl |
| Primer (forward and reverse) | 250 nM | 0.0625 µl of each 100 umole stock |
| ddH$_2$O | N/A | 2.375. µl |
| Template DNA | 20 ng | 10.0 µl |
| Total | | 25 µl |

The cycling parameters for each amplicon are listed in Table 3.

TABLE 3

Cycling Parameters.

| Step | Temperature (° C.) | Duration |
|---|---|---|
| 1 | 95 | 3 min |
| 2 | 95 | 30 sec |
| 3 | 66 (3.4 deletion primers) or 61.5 (12 s primers) or 61.5 (TNF primers) | 30 sec |
| 4 | 72 | 30 sec |
| 5 | Plate Read | |
| 6 | 72 | 10 min |
| 7 | Melting Curve 50° C.-110° C. reading every 1° C. | 3 sec |

Repeat steps 2-5, 44 times for a total of 45 cycles.

Thermal cycling, real-time detection and analysis of the reactions was carried out using a DNA Engine Opticon® 2 Continuous Fluorescence Detection System equipped with Intuitive Opticon Monitor™ software (MJ Research Inc.). The standard curve method was utilized for DNA quantification. A set of serial dilutions ($10^6$, $10^5$, $10^4$, $10^3$, $10^2$, $10^1$) of three purified PCR generated templates, one product for the 3.4 deletion, one for the 12s primers, and one for TNF. From this, three different standard curves were generated showing the number of copies of total mtDNA (12s amplicon-total mitochondrial genome primers), the amount of mtDNA having the 3.4 kb deletion, or total nuclear DNA (TNF-single copy nuclear gene primers). The $C_T$ values of the samples were then converted to the number of DNA copies by comparing the sample $C_T$ to that of the standards. The 3.4 deletion was considered to be absent or at low levels if the deletion was not detected within 37 cycles.

The determination of malignancy is based upon the quantity of the 3.4 kb deletion present in the normalized sample as indicated by the location of the cycle threshold. This location may be either absolute, as in greater than 25 cycles but less than 35 cycles, or more likely a ratio between the total mitochondrial DNA present as indicated by the 12s amplicon, and the 3.4 kb deletion. This may be expressed as a percent of the total mitochondrial DNA. The number of cells, as represented by the TNF amplicon, may be incorporated to refine the distinction between benign and malignant tissues.

In order to automate the analyses of these samples, bioinformatics tools were employed. The three variables that were considered for these analyses were the cycle threshold $C_T$ of Tumour Necrosis Factor (TNF), total pieces of mitochondria that contain those specific primer sites, and those mitochondria that harbour the deletion of interest.

Cluster Analysis

The clustering was not normalized nor were logarithmic functions used due to the similar and small range of data.

Figure 3:
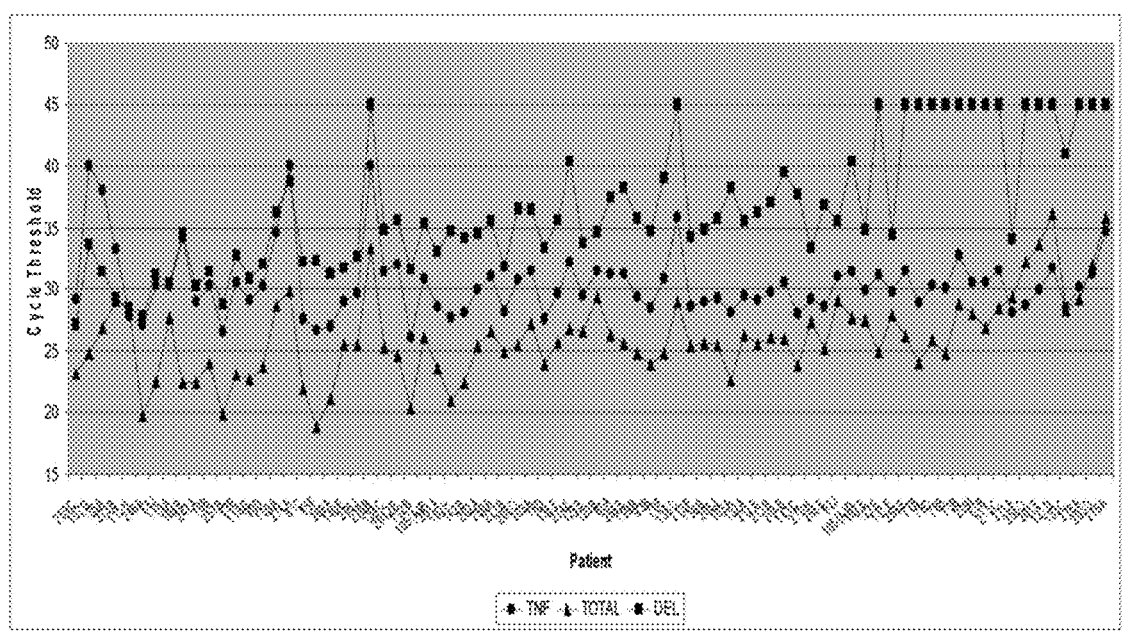
FIG. 3 is a graph showing cycle threshold as related to Example 1.
Figure 4:
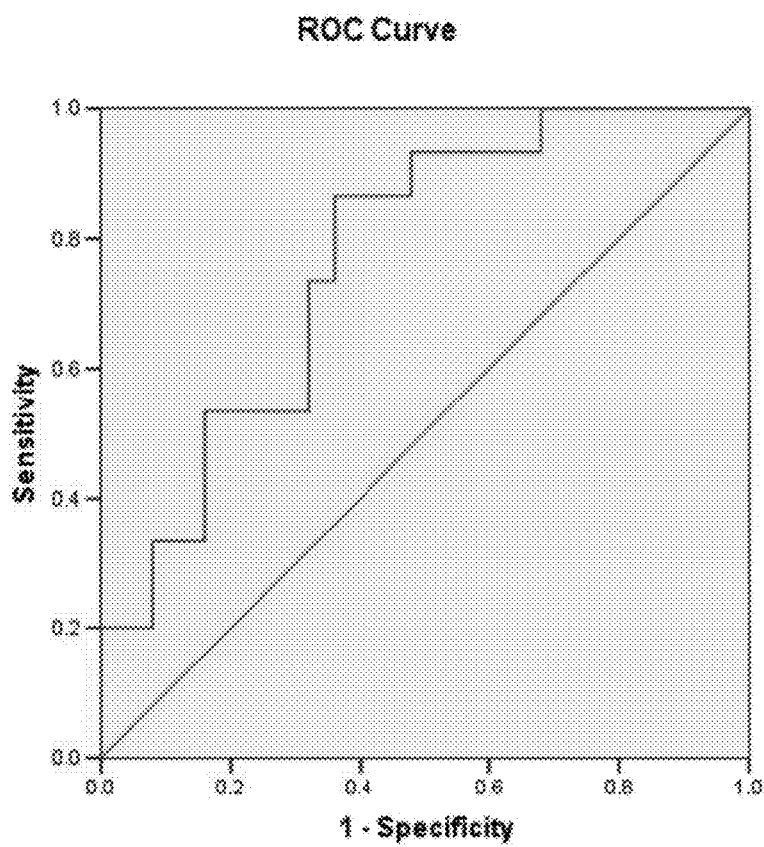
FIG. 4 shows a ROC curve illustrating the specificity and sensitivity of one embodiment of the present invention.

FIG. 3 shows the actual movement and trends of the data. The x-axis is the patient number and the y-axis is the cycle threshold obtained from real time PCR.

It is important to note that the higher the cycle threshold is, the lower amount of the deletion is present.

The general trend shown in FIG. 3 is based upon the differences/ratios between the variables of Deletion, Total, and TNF. The deletion is low to absent for the benign/normal samples (right side) and increases (toward the left) with abnormal benign and malignant samples. The abnormal benign and malignant samples begin to differentiate themselves from each other based on the cycle threshold ratio of Deletion to TNF.

Supervised Learning

Supervised learning is based on the system trying to predict outcomes for known samples. Half of the data was used to train and the other half to test the algorithm. Supervised learning compares its predictions to the target answer and "learns" from its mistakes. But, if the predicted output is higher or lower than the actual outcome in the data, the error is propagated back through the system and the weights are adjusted accordingly.

Data SET: 5% to 35%—Benign
35% to 65%—Hyperplasia
65% to 95%—Malignant

Artificial Neural Network (ANN) Algorithm (shown schematically below):

Half of Data set used for Training ANN
Other half used to compare the accuracyAccuracy = Compare expected data set with obtained data set → 86.6%

Artificial Neural Network algorithm

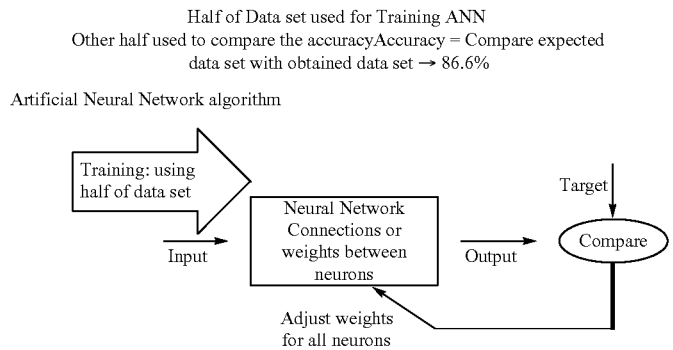

Supervised Learning of Deletion Data using Artificial Neural Network (ANN)

Three Classifications:
Benign
Hyperplasia
Malignant

Three variables for each classification were used based on Real Time PCR Cycle Threshold $C_T$:

Tumour Necrosis Factor (TNF)—Nuclear copy control.
Total Mitochondria—Mitochondria copy control
Deletion—Mitochondria in the deleted state.

Results:
Half of data set is used to train the ANN, and the remaining half is used to compare the accuracy.
Three Classification Accuracy=86.6%
Positive Predictive Value (PPV);
Benign to Malignant=88.2%
Negative Predictive Value (NPV)
Benign to Malignant=76.5%

Example 4: 3.4 kb Deletion in mtDNA Associated with Breast Cancer 18 samples were tested from malignant and benign breast tissue, 9 being malignant and 9 being benign, for the presence of the aforementioned 3.4 kb deletion. Samples were classified as either malignant or benign using conventional histopathological analysis.

DNA was isolated and purified from the samples using a QIAamp® DNA Mini Kit (Qiagen, Cat. #51304) according to manufacturer's specifications.

Purified oligonucleotide primers were chemically synthesized by Invitrogen (California, USA). The sequences of the primers and the expected sizes of the PCR products amplified are listed in Table 1 above.

Real-Time Polymerase Chain Reaction

Three separate PCRs were performed on each sample. Each reaction was 25 µl total volume and included template DNA, one pair of primers (12s or 3.4 Deletion or TNF), an iQ™ SYBR Green Supermix kit (Catalogue Number 170-8882, Bio-Rad Laboratories Inc.) and distilled deionized water (ddH$_2$O). The TNF (tumor necrosis factor) comprised single copy nuclear gene primers, and 12s comprised total mitochondrial genome primers. The volume and concentrations for template DNA, primers, and reaction buffer are listed below:

TABLE 4 qPCR Components.

| Reagent | Concentration per Reaction | Volume per Reaction |
| --- | --- | --- |
| Reaction Buffer | 1X | 12.5 µl |
| Primer (forward and reverse) | 250 nM | 0.0625 µl of each 100 µmole stock |
| ddH$_2$O | N/A | 2.375. µl |
| Template DNA | 20 ng | 10.0 µl |
| Total | | 25 µl |

The cycling parameters for each amplicon are listed in Table 5.

TABLE 5

Cycling Parameters.

| Step | Temperature (° C.) | Duration |
| --- | --- | --- |
| 1 | 95 | 3 min |
| 2 | 95 | 30 sec |
| 3 | 66 (3.4 deletion primers) or 61.5 (12 s primers) or 61.5 (TNF primers) | 30 sec |
| 4 | 72 | 30 sec |
| 5 | Plate Read | |
| 6 | 72 | 10 min |
| 7 | Melting Curve 50° C.-110° C. reading every 1° C. | 3 sec |

Repeat steps 2-5, 44 times for a total of 45 cycles.

Thermal cycling, real-time detection and analysis of the reactions was carried out using a DNA Engine Opticon® 2 Continuous Fluorescence Detection System equipped with Intuitive Opticon Monitor™ software (MJ Research Inc.). The standard curve method was utilized for DNA quantification. A set of serial dilutions ($10^6$, $10^5$, $10^4$, $10^3$, $10^2$, $10^1$) of three purified PCR generated templates were performed, one product for the 3.4 deletion, one for the 12s primers, and one for TNF. From this, three different standard curves were generated showing the number of copies of total mtDNA (12s amplicon-total mitochondrial genome primers), 3.4 deletion or total nuclear DNA (TNF-single copy nuclear gene primers). The $C_T$ values of the samples were then converted to the number of DNA copies by comparing the sample $C_T$ to that of the standards.

The determination of malignancy was based upon the quantity of the 3.4 kb deletion present in the normalized sample as indicated by the location of the cycle threshold. This location may be either absolute, as in greater than 25 cycles but less than 30 cycles, or more likely a ratio between the total mitochondrial DNA present as indicated by the 12s amplicon, and the 3.4 kb deletion. This may be expressed as a percent of the total mitochondrial DNA.

In order to automate the analyses of these samples, bioinformatics tools were employed. The three variables that were considered for these analyses were the cycle threshold $C_T$ of Tumour Necrosis Factor (TNF), total species of mitochondria that contain those specific primer sites, and those mitochondria that harbour the deletion of interest.

Figure 7:
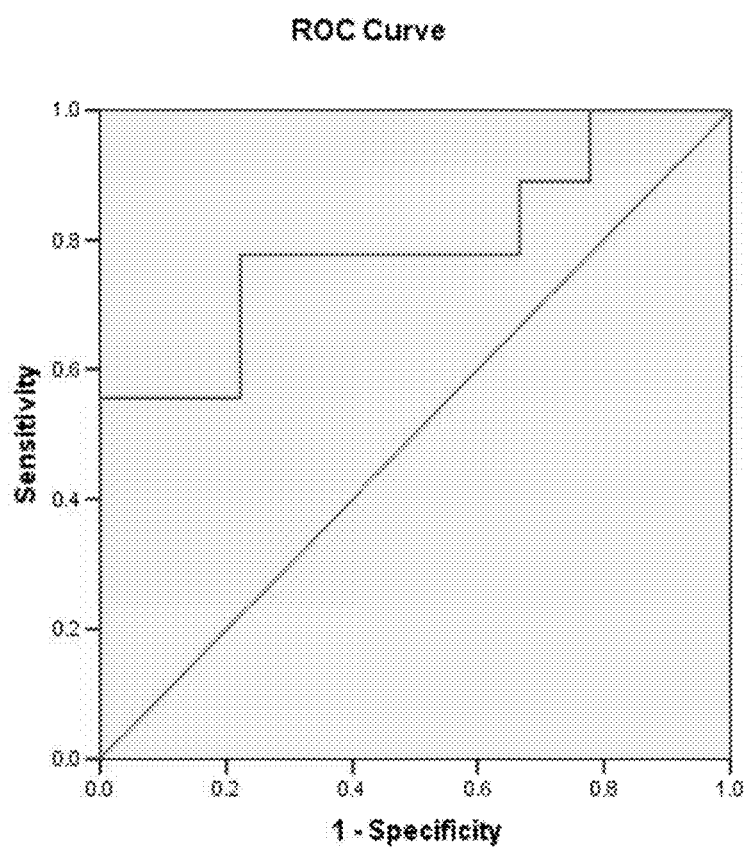

Table 6 and FIG. 7 show the difference in the mean $C_T$ scores for samples from malignant tissue and benign tissue. The mean $C_T$ value for normal tissue was 30.5889, while the mean $C_T$ for malignant tissue was 27.8533 thereby illustrating a difference in the quantity of mtDNA having the 3.4 kb deletion in malignant breast tissue compared to normal breast tissue.

TABLE 6

Mean values for $C_T$ scores
Group Statistics

| | GRP | N | Mean | Std. Deviation | Std. Error Mean |
|---|---|---|---|---|---|
| del3.4 | normal | 9 | 30.5889 | 2.53897 | .84632 |
| | malignant | 9 | 27.8533 | 2.52253 | .84084 |

FIG. 8 is an ROC curve illustrating the specificity and sensitivity of the 3.4 kb mtDNA deletion as a marker for breast cancer when testing breast tissue. These results were obtained using a cutoff $C_T$ of 29.1900. The sensitivity of the marker at this $C_T$ was 77.8%, while the specificity was 77.8%.

Table 7 shows the calculation of the area under the curve for the present example. As a measure of the accuracy of the test.

TABLE 7

Results Showing Area Under the Curve
Area Under the Curve
Test Result Variable(s): del3.4

| Area | Std. Error[a] | Sig.[b] | Asymptotic 95% Confidence Interval | |
|---|---|---|---|---|
| | | | Lower Bound | Upper Bound |
| .790 | .112 | .038 | .570 | 1.010 |

[a]Under the nonparametric assumption
[b]Null hypothesis: true area = 0.5

The determination of the cutoff $C_T$ of 29.1900 is shown in table 8 below. The results listed in table 8 show that a cutoff $C_T$ of 29.1900 provided the highest sensitivity and specificity at 78% and 78% respectively.

TABLE 8

Determination of $C_T$ cutoff.
Coordinates of the Curve
Test Result Variable(s): del3.4

| Positive if Less Than or Equal To[a] | Sensitivity | 1 − Specificity |
|---|---|---|
| 24.6000 | .000 | .000 |
| 25.6800 | .111 | .000 |
| 25.7700 | .222 | .000 |
| 25.9250 | .333 | .000 |
| 26.2050 | .444 | .000 |
| 26.8400 | .556 | .000 |
| 27.4800 | .556 | .111 |
| 28.1600 | .556 | .222 |
| 28.8800 | .667 | .222 |
| 29.1900 | .778 | .222 |
| 29.4600 | .778 | .333 |
| 29.8750 | .778 | .444 |
| 30.5850 | .778 | .556 |
| 31.2200 | .778 | .667 |
| 31.5000 | .889 | .667 |
| 31.7650 | .889 | .778 |
| 32.9900 | 1.000 | .778 |
| 34.3350 | 1.000 | .889 |
| 35.6400 | 1.000 | 1.000 |

[a]The smallest cutoff value is the minimum observed test value minus 1, and the largest cutoff value is the maximum observed test value plus 1. All the other cutoff values are the averages of two consecutive ordered observed test values.

Example 5: The 3.4 kb Deletion in the Prostate Massage Fluid of Individuals with Prostate Cancer as Compared to the Fluid from Those without Histological Evidence of Prostate Cancer Forty prostate massage fluid samples were collected by urologists from patients who were either subsequently diagnosed with prostate cancer or showed no histological evidence of prostate cancer following a prostate needle biopsy procedure. The sample was deposited on a IsoCode Card™ (Schleicher & Shuell), dried, and then extracted according to the manufacturer's protocol. All DNA extracts were quantified using a NanoDrop™ ND-1000 Spectrophotometer and the DNA concentration normalized to 2 ng/ul. Each sample was then amplified according to the following parameters:

```
1X iQ SYBR Green Supermix ™ (Bio-Rad P/N
170-8880)
150nmol forward primer
                                    (SEQ ID NO: 2)
(5'-TAGACTACGTACATACTAACCCTACTCCTA-3').

150 nmol reverse primer
                                    (SEQ ID NO: 3)
(5'-GAGGTAGGATTGGTGCTGT-3')
20 ng template DNA in a 25 ul reaction.
```

Reactions were cycled on an Opticon™ 2 DNA Engine (Bio-Rad Canada) according to the following protocol:

1. 95° C. for 3 minutes
2. 95° C. for 30 seconds
3. 66° C. for 30 seconds
4. 72° C. for 30 seconds
5. Plate Read
6. Repeat steps 2-5 44 times
7. 72° C. for 10 minutes 8. Melting Curve from 50° C. to 105° C., read every 1° C., hold for 3 seconds
9. 10° C. Hold

TABLE 9

Results showing the mean $C_T$ Values for Prostate Massage Fluid Test
Group Statistics

| | Group | N | Mean | Std. Deviation | Std. Error Mean |
|---|---|---|---|---|---|
| DEL3.4 | benign | 25 | 37.1869 | 3.18495 | .63699 |
| | malignant | 15 | 33.7712 | 3.98056 | 1.02778 |

Tables 9 and 10 show a significant difference between the mean $C_T$ values obtained for the benign sample and the malignant sample groups (p=0.005).

TABLE 10

Results Showing Difference (p = 0.005) for $C_T$ values of samples.
Independent Samples Test

| | | Levene's Test for Equality of Variances | | t-test for Equality of Means | | | | | 95% Confidence Interval of the Difference | |
|---|---|---|---|---|---|---|---|---|---|---|
| | | F | Sig. | t | df | Sig. (2 tailed) | Mean Difference | Std. Error Difference | Lower | Upper |
| DEL3.4 | Equal variances assumed | 1.251 | .270 | 2989 | 38 | .005 | 3.41570 | 1.14283 | 1.10217 | 5.72923 |
| | Equal variances not assumed | | | 2825 | 24.696 | .009 | 3.41570 | 1.20917 | .92382 | 5.90758 |

Figure 5:
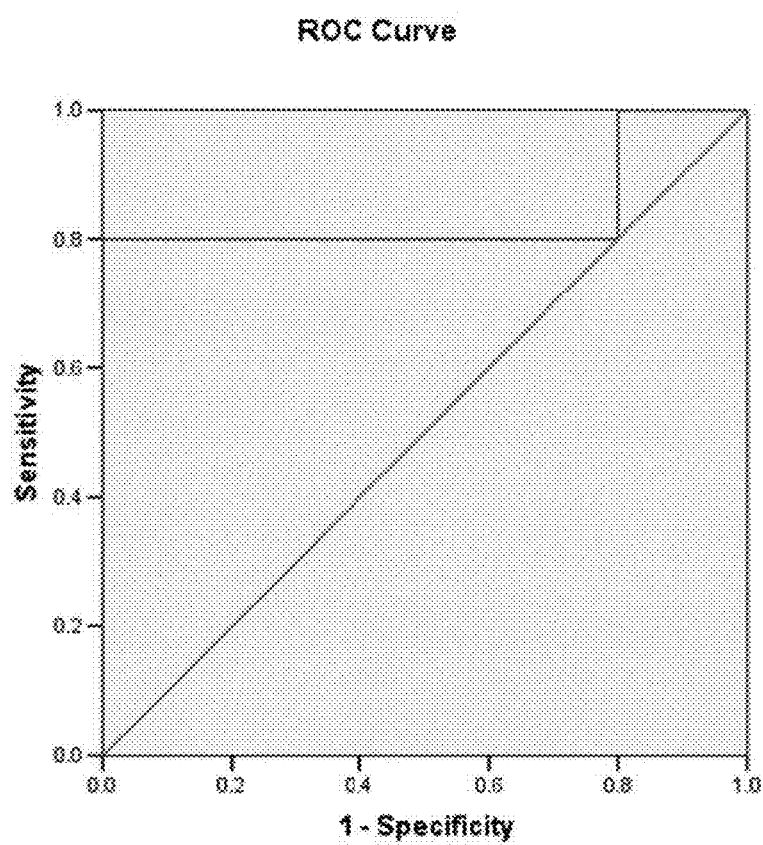
FIG. 5 shows a ROC curve illustrating the specificity and sensitivity of another embodiment of the present invention.

FIG. 5 is a Receiver Operating Characteristic (ROC) curve illustrating the specificity and sensitivity of the 3.4 kb mtDNA deletion as a marker for prostate cancer when testing prostate massage fluid. These results were obtained using a cutoff $C_T$ of 37.3683. The sensitivity of the marker at this $C_T$ is 87%, while the specificity is 64%.

The accuracy of the test depends on how well the test separates the group being tested into those with and without the prostate cancer. Accuracy is measured by the area under the ROC curve. Table 11 shows the calculation of the area under the curve for the present example.

TABLE 11

Results Showing Area Under the ROC Curve
Area Under the Curve
Test Result Variable(s): DEL3.4

| Area | Std. Error[a] | Sig.[b] | Asymptotic 95% Confidence Interval | |
|---|---|---|---|---|
| | | | Lower Bound | Upper Bound |
| .768 | .074 | .005 | .622 | .914 |

[a]Under the nonparametric assumption
[b]Null hypothesis: true area = 0.5

TABLE 12

Determination of Specificity and Sensitivity
Coordinates of the Curve
Test Result Variable(s): DEL3.4

| Positive if Less Than or Equal To[a] | Sensitivity | 1 − Specificity |
|---|---|---|
| 26.2992 | .000 | .000 |
| 27.3786 | .067 | .000 |
| 28.2484 | .133 | .000 |
| 29.5193 | .200 | .000 |
| 30.1757 | .200 | .040 |
| 30.4580 | .200 | .080 |
| 30.5980 | .267 | .080 |
| 31.5709 | .333 | .080 |
| 32.5712 | .333 | .120 |

TABLE 12-continued

Determination of Specificity and Sensitivity
Coordinates of the Curve
Test Result Variable(s): DEL3.4

| Positive if Less Than or Equal To[a] | Sensitivity | 1 − Specificity |
|---|---|---|
| 32.9500 | .333 | .160 |
| 33.3314 | .400 | .160 |
| 33.6547 | .467 | .160 |
| 33.9247 | .533 | .160 |
| 34.3554 | .533 | .200 |
| 34.9056 | .533 | .240 |
| 35.4650 | .533 | .280 |
| 35.9172 | .533 | .320 |
| 36.0648 | .600 | .320 |
| 36.3616 | .667 | .320 |
| 36.6421 | .733 | .320 |
| 36.8531 | .733 | .360 |
| 37.1188 | .800 | .360 |
| 37.3683 | .867 | .360 |
| 37.5200 | .867 | .400 |
| 37.8341 | .867 | .440 |
| 38.2533 | .867 | .480 |
| 38.5198 | .933 | .480 |
| 38.6519 | .933 | .520 |
| 38.8552 | .933 | .560 |
| 39.1258 | .933 | .600 |
| 39.2734 | .933 | .640 |
| 39.4952 | .933 | .680 |
| 39.7323 | 1.000 | .680 |
| 39.6956 | 1.000 | .720 |
| 41.0000 | 1.000 | 1.000 |

The smallest cutoff value is the minimum observed test value −1, and the largest cutoff value is the maximum observed test value plus 1. All the other cutoff values are the average of two consecutive ordered, observed test values.

The determination of the cutoff $C_T$ of 37.3683 is shown in table 12 above. The results listed in table 12 illustrate that a cutoff $C_T$ of 37.3683 provided the highest sensitivity and specificity.

Example 6: The 3.4 kb Deletion in the Urine of Individuals with Prostate Cancer as Compared to the Fluid from Those without Histological Evidence of Prostate Cancer Urine samples were collected from 5 patients who were diagnosed with prostate cancer and 5 who have had a needle biopsy procedure which was unable to detect prostate malignancy. These samples were collected following a digital rectal exam (DRE) to facilitate the collection of prostate cells.

Upon receipt of the samples a 5 ml aliquot was removed and then 2 mls were centrifuged at 14,000×g to form a pellet. The supernatant was removed and discarded. Pellets were resuspended in 200 ul phosphate buffered saline solution. Both the resuspended pellet and the whole urine sample were subjected to a DNA extraction procedure using the QiaAMP™ DNA Mini Kit (Qiagen P/N 51304) according to the manufacturer's directions. The resulting DNA extracts were then quantified using a NanoDrop™ ND-1000 Spectrophotometer and normalized to a concentration of 0.1 ng/ul.

Samples were analyzed by quantitative real-time PCR with the 3.4 kb deletion specific primers according to the following:

```
1X iQ SYBR Green Supermix ™ (Bio-Rad P/N
170-8880)
100 nmol forward primer
                              (SEQ ID NO: 2)
(5'-TAGACTACGTACATACTAACCCTACTCCTA-3')

100 nmol reverse primer
                              (SEQ ID NO: 3)
(5'-GAGGTAGGATTGGTGCTGT-3')
1 ng template DNA in a 25 ul reaction.
```

Reactions were cycled on an Opticon™ 2 DNA Engine (Bio-Rad Canada) according to the following protocol:

1. 95° C. for 3 minutes
2. 95° C. for 30 seconds
3. 69° C. for 30 seconds
4. 72° C. for 30 seconds
5. Plate Read
6. Repeat steps 2-5 44 times
7. 72° C. for 10 minutes
8. Melting Curve from 50° C. to 105° C., read every 1° C., hold for 3 seconds
9. 10° C. Hold

TABLE 13

Mean values for $C_T$ scores
Group Statistics

|  | GRPfluid38 | N | Mean | Std. Deviation | Std. Error Mean |
|---|---|---|---|---|---|
| CTf | Benign | 5 | 33.2780 | 1.10900 | .49596 |
|  | Malignant | 5 | 30.6980 | 2.55767 | 1.14382 |

Tables 13 and 14 show a significant difference between the mean $C_T$ values obtained for benign sample and the malignant sample groups (p=0.005).

TABLE 14

Results Showing Difference (p = 0.005) for $C_T$ values of samples.
Independent Samples Test

| | | Levene's Test for Equality of Variances | | t-test for Equality of Means | | | | | 95% Confidence Interval of the Difference | |
|---|---|---|---|---|---|---|---|---|---|---|
| | | F | Sig. | t | df | Sig. (2 tailed) | Mean Difference | Std. Error Difference | Lower | Upper |
| DEL3.4 | Equal variances assumed | 1272 | .292 | 2069 | 8 | 0.72 | 258000 | 124672 | −29494 | 545494 |
| | Equal variances not assumed | | | 2069 | 5.453 | .089 | 258000 | 124672 | −.54639 | 570639 |

Figure 6:
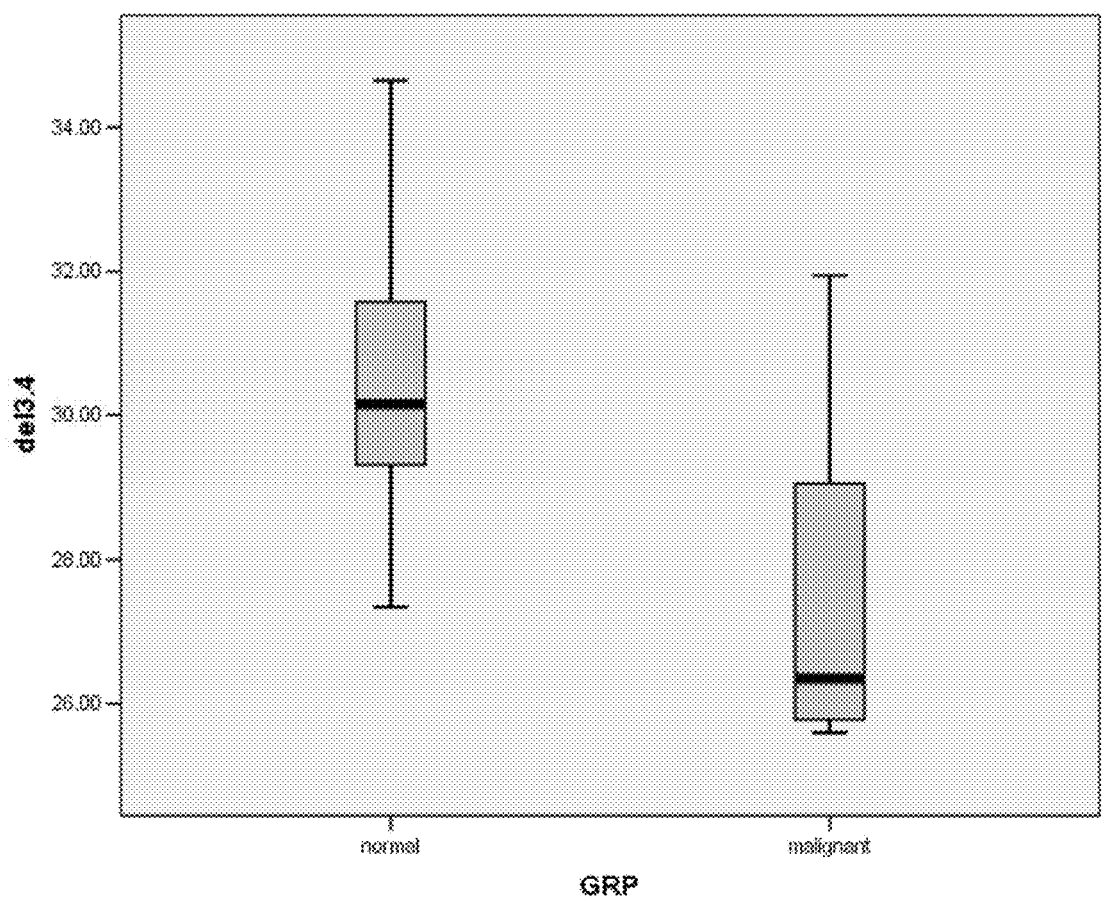
FIG. 6 shows real-time PCR data relating to 3.4 kb mtDNA deletion levels associated with breast cancer; and, FIG. 7 shows a ROC curve illustrating the specificity and sensitivity of another embodiment of the present invention.

FIG. 6 is a Receiver Operating Characteristic (ROC) curve illustrating the specificity and sensitivity of the 3.4 kb mtDNA deletion as a marker for prostate cancer when testing urine. These results were obtained using a cutoff $C_T$ of 31.575. The sensitivity of the marker at this $C_T$ is 80%, while the specificity is 100%.

The determination of the cutoff $C_T$ of 31.575 is shown in table 15. The results listed in table 15 show that a cutoff $C_T$ of 31.575 provided the highest sensitivity and specificity.

TABLE 15

Determination of $C_T$ cutoff.
Coordinates of the Curve
Test Result Variable(s): CTf

| Positive if Less Than or Equal To[a] | Sensitivity | 1 − Specificity |
|---|---|---|
| 26.2900 | .000 | .000 |
| 28.4950 | .200 | .000 |
| 30.3850 | .400 | .000 |
| 31.0800 | .600 | .000 |

TABLE 15-continued

Determination of $C_T$ cutoff.
Coordinates of the Curve
Test Result Variable(s): CTf

| Positive if Less Than or Equal To[a] | Sensitivity | 1 − Specificity |
|---|---|---|
| 31.5750 | .800 | .000 |
| 32.1400 | .800 | .200 |
| 32.8150 | .800 | .400 |
| 33.8700 | .800 | .600 |
| 34.3350 | .800 | .800 |
| 34.3550 | 1.000 | .800 |
| 35.3700 | 1.000 | 1.000 |

[a] The smallest cutoff value is the minimum observed test value minus 1, and the largest cutoff value is the maximum observed test value plus 1. All the other cutoff values are the averages of two consecutive ordered observed test values.

Example 7: Detection of Re-Circularized 3.4 kb Deleted Sequence in Prostate Malignant and Benign Tissue In this example, the amount of re-circularized 3.4 kb deleted mtDNA molecules in samples was tested as an indicator for prostate cancer. As mentioned above, the 3.4 kb sequence, upon deletion, may reform as a circular mtDNA molecule. Amplification of a target region from the deleted 3.4 kb mtDNA sublimon was conducted using a primer pair (SEQ ID NOS: 9 and 10). The forward primer (SEQ ID NO: 9), overlaps the rejoining site of the ends of the 3.4 kb sequence.

Prostate tissue was formalin-fixed paraffin embedded prostate tissue needle biopsies.

The reagent setup used for this example was as follows:
250 nmol each primer
12.5 ul of 2× reaction mix,
20 ng (10 ul of 2 ng/ul) template in 25 ul reaction volume.

The cycling parameters were as follows:
1. 95 degrees Celsius for 3 minutes
2. 95 degrees Celsius for 30 seconds
3. 62 degrees Celsius for 30 seconds
4. 72 degrees Celsius for 30 seconds
5. Plate Read
6. Repeat steps 2-5 44 times
7. 72 degrees for 10 minutes
8. Melting Curve from 50-100 degrees, reading every 1 degree for 3 seconds
9 4 degrees HOLD.

Amplification of a target region from the deleted 3.4 kb mtDNA sublimon was conducted using a primer pair (SEQ ID NOS: 9 and 10).

Table 16 below provides a summary of testing conducted for the detection of the actual 3.4 kb deleted in mtDNA obtained from malignant and benign prostate tissue. Using a $C_T$ score of 30.0, a clear identification of malignant and benign tissue was possible. As such, an increase in the amount of the 3.4 kb molecule present in a sample was indicative of cancer.

TABLE 16

$C_T$ scores for Detection of Cancer in Prostate Tissue

| Description | $C_T$ |
|---|---|
| Benign sample 1 | 33.75 |
| Malignant sample 1 | 28.79 |
| Benign sample 2 | 30.96 |
| Malignant sample 2 | 28.4 |
| Benign sample 3 | 32.19 |
| Malignant sample 3 | 27.38 |

Although the invention has been described with reference to certain specific embodiments, various modifications thereof will be apparent to those skilled in the art without departing from the spirit and scope of the invention as outlined in the claims appended hereto.

REFERENCES

Birch-Machin M A, Online Conference Report (Sunburnt DNA), International Congress of Biochemistry and Molecular Biology, New Scientist, 2000(a)

Birch-Machin M A, Taylor R W, Cochran B, Ackrell B A C, Turnbull D M. Ann Neurol 48: 330-335, 2000(b)

Birch-Machin, M. A. (2000). Mitochondria and skin disease. Clin Exp Dermatol, 25, 141-6.

Brown, M. D., et al., Am J. Humn Genet, 60: 381-387, 1997

Bogliolo, M, et al., Mutagenesis, 14: 77-82, 1999

Chinnery P F and Turnbull D M., Lancet 354 (supplement 1): 17-21, 1999

Huoponen, Kirsi, Leber hereditary optic neuropathy: clinical and molecular genetic findings, Neurogenetics (2001) 3: 119-125.

Hayward S W, Grossfeld G D, Tlsty T D, Cunha G R., Int J Oncol 13:35-47, 1998

Huang G M, Ng W L, Farkas J, He L, Liang H A, Gordon D, Hood R., Genomics 59(2):178-86, 1999

Konishi N, Cho M, Yamamoto K, Hiasa Y. Pathol. Int. 47:735-747, 1997

Landis S H, Murray T, Bolden S, Wingo P A. Cancer J. Clin. 49:8-31

Lee H C, Lu C Y, Fahn H J, Wei YHu. Federation of European Biochemical Societies, 441:292-296, 1998

Mitochondrial Research Society http://www.mitoresearch.org/diseases.html.

MITOMAP: A human mt genome database (www.gen.emory.edu/mitomap.html).

Naviaux, R K., Mitochondrial Disease—Primary Care Physican's Guide. Psy-Ed. Corp D/B/A Exceptional Parents Guide: 3-10, 1997

Parrella P, Xiao Y, Fliss M, Sanchez-Cespedes M, Mazzarelli P, Rinaldi M, Nicol T, Gabrielson E, Cuomo C, Cohen D, Pandit S, Spencer M, Rabitti C, Fazio V M, Sidransky D: Detection of mitochondrial DNA mutations in primary breast cancer and fine-needle aspirates. Cancer Res 2001, 61:7623-7626

Polyak Y, et al., Nature Genet. 20 (3):291-293, 1998

Seidman, M. D. et al., Arch. Otolaryngol Head Neck Surg., 123: 1039-1045, 1997

Sherrat E J, Thomas A W, Alcolado J C., Clin. Sci. 92:225-235, 1997

Shoffner J M, Brown M D, Torroni A, Lott M T, Cabell M F, Mirra S S, Beal M F, Yang C, Gearing M, Salvo R, Watts R L, Juncos J L, Hansen L A, Crain B J, Fayad M, Reckford C L, and Wallace D C., Genomics 17: 171-184, 1993

SpringNet—C E Connection: Screening, Diagnosis: Improving Primary Care Outcomes. Website: http://www.springnet.com/ce/j803a.htm Taniike, M. et al., BioChem BioPhys Res Comun, 186: 47-53, 1992

Valnot, Isabelle, et al., A mitochondrial cytochrome b mutation but no mutations of nuclearly encoded subunits in ubiquinol cytochrome c reductase (complex III) deficiency, *Human Genetics* (1999) 104: 460-466 von Wurmb, N, Oehmichen, M, Meissner, C., *Mutat Res.* 422:247-254, 1998

Wallace et al., Mitochondiral DNA MUtatio Assoicated with Leber's Hereditary Optic Neuropathy, *Science*, 1427-1429

Wei Y H. Proceedings of the Nat. Sci. Council of the Republic of China April 22(2):5567, 1998

Woodwell D A. National Ambulatory Medical Care Survey: 1997 Summary. Advance data from vital and health statistics; no. 305. Hyattsville, Md.: National Center for Health Statistics. 1999

Yeh, J. J., et al., *Oncogene Journal*, 19: 2060-2066, 2000

Zhang et al., Multiple mitochondiral DNA deletions in an elderly human individual, *FEBS Lett*, 297, 34-38 1992

Zhang, C., et al., *BioChem. BioPhys. Res. Comun.*, 195: 1104-1110, 1993

---

What we claim is:

1. A method of detecting a cancer in an individual, the method comprising:
   a) obtaining a biological sample from the individual;
   b) quantifying the amount of mtDNA in the sample having a deletion in the nucleic acid sequence spanning approximately residues 10744 and 14124 of the mtDNA genome, wherein the step of quantifying comprises contacting the sample with a pair of amplification primers and amplifying a target region of mtDNA that is indicative of the deletion, wherein a first primer of the pair of primers is adapted to bind to a region of the mtDNA comprising a splice joining opposite ends of the mtDNA sequence after removal of the deletion;
   c) comparing the amount of mtDNA in the sample having the deletion to the amount of the deletion in a reference sample of mtDNA wherein the reference sample is from a known non-cancerous tissue or body fluid or from a known cancerous tissue or body fluid;
   wherein if the reference sample is from a known non-cancerous tissue or body fluid, then an elevated level of the deletion in the biological sample compared to the non-cancerous reference sample is indicative of cancer and if the reference sample is from a known cancerous tissue or body fluid sample then an equivalent or elevated level of the deletion in the biological sample compared to the cancerous reference sample is indicative of cancer.

2. The method of claim 1 wherein the deletion has the nucleic acid sequence set forth in SEQ ID NO: 1.

3. The method of claim 1, wherein the first primer has the nucleic acid sequence set forth in SEQ ID NO: 2.

4. The method of claim 1 wherein the step of quantifying is conducted using real-time PCR.

5. The method of claim 1 wherein the cancer is prostate cancer.

6. The method of claim 1 wherein the cancer is breast cancer.

7. The method of claim 1 wherein the biological sample is a body tissue or body fluid.

8. The method of claim 7 wherein the biological sample is breast tissue, prostate tissue, prostate massage fluid, or urine.

9. A method of monitoring an individual for the development of a cancer, the method comprising;
   a) obtaining a biological sample from the individual;
   b) quantifying the amount of mtDNA in the sample having a deletion in the nucleic acid sequence spanning approximately residues 10744 and 14124 of the mtDNA genome, wherein the step of quantifying comprises contacting the sample with a pair of amplification primers and amplifying a target region of mtDNA that is indicative of the deletion, wherein a first primer of the pair of primers is adapted to bind to a region of the mtDNA comprising a splice joining opposite ends of the mtDNA sequence after removal of the deletion;
   c) repeating steps a) to b) over a duration of time; and
   d) wherein an increasing level of the deletion over the duration of time is indicative of cancer.

10. The method of claim 9, wherein the deletion has the nucleic acid sequence set forth in SEQ ID NO: 1.

11. The method of claim 9, further comprising at least one step selected from the group consisting of: (a) comparing the amount of mtDNA in the sample having the deletion to the amount of the deletion in a reference sample of mtDNA from known non-cancerous tissue or body fluid; and (b) comparing the amount of mtDNA in the sample having the deletion to the amount of the deletion in a reference sample of mtDNA from known cancerous tissue or body fluid.

12. The method of claim 9 wherein the step of quantifying is conducted using real-time PCR.

13. The method of claim 9, wherein the first primer has the nucleic acid sequence set forth in SEQ ID NO: 2.

14. The method of claim 9 wherein the cancer is prostate cancer.

15. The method of claim 9 wherein the cancer is breast cancer.

16. The method of claim 9 wherein the biological sample is a body tissue or body fluid.

17. The method of claim 16 wherein the biological sample is breast tissue, prostate tissue, prostate massage fluid, or urine.

* * * * *

SEQUENCE LISTING

```
<160> NUMBER OF SEQ ID NOS: 10

<210> SEQ ID NO 1
<211> LENGTH: 3379
<212> TYPE: DNA
<213> ORGANISM: Homo sapiens

<400> SEQUENCE: 1
cctaaaccta ctccaatgct aaaactaatc gtcccaacaa ttatattact accactgaca      60
tgactttcca aaaaacacat aatttgaatc aacacaacca cccacagcct aattattagc     120
atcatccctc tactattttt taaccaaatc aacaacaacc tatttagctg ttccccaacc     180
ttttcctccg accccctaac aaccccctc ctaatactaa ctacctgact cctacccctc     240
acaatcatgg caagccaacg ccacttatcc agtgaaccac tatcacgaaa aaaactctac     300
ctctctatac taatctccct acaaatctcc ttaattataa cattcacagc cacagaacta     360
atcatatttt atatcttctt cgaaaccaca cttatcccca ccttggctat catcacccga     420
tgaggcaacc agccagaacg cctgaacgca ggcacatact tcctattcta caccctagta     480
ggctcccttc ccctactcat cgcactaatt tacactcaca acaccctagg ctcactaaac     540
attctactac tcactctcac tgcccaagaa ctatcaaact cctgagccaa caacttaata     600
tgactagctt acacaatagc tttttatagta aagatacctc tttacggact ccacttatga     660
ctccctaaag cccatgtcga agccccccatc gctgggtcaa tagtacttgc cgcagtactc     720
ttaaaactag gcggctatgg tataatacgc ctcacactca ttctcaaccc cctgacaaaa     780
cacatagcct accccttcct tgtactatcc ctatgaggca taattataac aagctccatc     840
tgcctacgac aaacagacct aaaatcgctc attgcatact cttcaatcag ccacatagcc     900
ctcgtagtaa cagccattct catccaaacc ccctgaagct tcaccggcgc agtcattctc     960
ataatcgccc acgggcttac atcctcatta ctattctgcc tagcaaactc aaactacgaa    1020
cgcactcaca gtcgcatcat aatcctctct caaggacttc aaactctact cccactaata    1080 gcttttgat gacttctagc aagcctcgct aacctcgcct taccccccac tattaaccta    1140
ctgggagaac tctctgtgct agtaaccacg ttctcctgat caaatatcac tctcctactt    1200
acaggactca acatactagt cacagcccta tactccctct acatatttac cacaacacaa    1260
tggggctcac tcacccacca cattaacaac ataaaaccct cattcacacg agaaaacacc    1320
ctcatgttca tacacctatc ccccattctc ctcctatccc tcaacccga catcattacc    1380 gggtttcct cttgtaaata tagtttaacc aaaacatcag attgtgaatc tgacaacaga    1440
ggcttacgac cccttattta ccgagaaagc tcacaagaac tgctaactca tgcccccatg    1500
tctaacaaca tggctttctc aacttttaaa ggataacagc tatccattgg tcttaggccc    1560
```

```
caaaaatttt ggtgcaactc caaataaaag taataaccat gcacactact ataaccaccc    1620
taaccctgac ttccctaatt cccccatcc ttaccacct cgttaaccct aacaaaaaaa      1680
actcataccc ccattatgta aaatccattg tcgcatccac ctttattatc agtctcttcc    1740
ccacaacaat attcatgtgc ctagaccaag aagttattat ctcgaactga cactgagcca    1800
caacccaaac aacccagctc tccctaagct tcaaactaga ctacttctcc ataatattca    1860
tccctgtagc attgttcgtt acatggtcca tcatagaatt ctcactgtga tatataaact    1920
cagacccaaa cattaatcag ttcttcaaat atctactcat cttcctaatt accatactaa    1980
tcttagttac cgctaacaac ctattccaac tgttcatcgg ctgagagggc gtaggaatta    2040
tatccttctt gctcatcagt tgatgatacg cccgagcaga tgccaacaca gcagccattc    2100
aagcaatcct atacaaccgt atcggcgata tcggtttcat cctcgcctta gcatgattta    2160
tcctacactc caactcatga gacccacaac aaatagccct tctaaacgct aatccaagcc    2220
tcaccccact actaggcctc ctcctagcag cagcaggcaa atcagcccaa ttaggtctcc    2280 accctgact cccctcagcc atagaaggcc ccaccccagt ctcagcccta ctccactcaa     2340
gcactatagt tgtagcagga atcttcttac tcatccgctt ccacccccta gcagaaaata    2400
gcccactaat ccaaactcta acactatgct taggcgctat caccactctg ttcgcagcag    2460
tctgcgccct tacacaaaat gacatcaaaa aaatcgtagc cttctccact tcaagtcaac    2520
taggactcat aatagttaca atcggcatca accaaccaca cctagcattc ctgcacatct    2580
gtacccacgc cttcttcaaa gccatactat ttatgtgctc cgggtccatc atccacaacc    2640
ttaacaatga acaagatatt cgaaaaatag gaggactact caaaaccata cctctcactt    2700
caacctccct caccattggc agcctagcat tagcaggaat cctttcctc acaggttttct    2760 actccaaaga ccacatcatc gaaaccgcaa acatatcata cacaaacgcc tgagccctat    2820
ctattactct catcgctacc tccctgacaa gcgcctatag cactcgaata attcttctca    2880
ccctaacagg tcaacctcgc ttccccaccc ttactaacat taacgaaaat aaccccaccc    2940
tactaaaccc cattaaacgc ctggcagccg gaagcctatt cgcaggattt ctcattacta    3000
acaacatttc ccccgcatcc cccttccaaa caacaatccc cctctaccta aaactcacag    3060
ccctcgctgt cactttccta ggacttctaa cagccctaga cctcaactac ctaaccaaca    3120
aacttaaaat aaaatcccca ctatgcacat tttatttctc caacatactc ggattctacc    3180
ctagcatcac acaccgcaca atcccctatc taggccttct tacgagccaa aacctgcccc    3240
tactcctcct agacctaacc tgactagaaa agctattacc taaaacaatt tcacagcacc    3300
aaatctccac ctccatcatc acctcaaccc aaaaaggcat aattaaactt tacttcctct    3360
ctttcttctt cccactcat                                                 3379
```

<210> SEQ ID NO 2
<211> LENGTH: 30
<212> TYPE: DNA
<213> ORGANISM: Artificial Sequence
<220> FEATURE:
<223> OTHER INFORMATION: synthetic primer 3.4 kb deletion forward

<400> SEQUENCE: 2
tagactacgt acatactaac cctactccta                                      30

<210> SEQ ID NO 3
<211> LENGTH: 19
<212> TYPE: DNA

```
<213> ORGANISM: Artificial Sequence
<220> FEATURE:
<223> OTHER INFORMATION: synthetic primer 3.4 kb deletion reverse

<400> SEQUENCE: 3
gaggtaggat tggtgctgt                                                    19

<210> SEQ ID NO 4
<211> LENGTH: 21
<212> TYPE: DNA
<213> ORGANISM: Artificial Sequence
<220> FEATURE:
<223> OTHER INFORMATION: synthetic primer mtDNA genome forward

<400> SEQUENCE: 4
cgttccagtg agttcaccct c                                                 21

<210> SEQ ID NO 5
<211> LENGTH: 23
<212> TYPE: DNA
<213> ORGANISM: Artificial Sequence
<220> FEATURE:
<223> OTHER INFORMATION: synthetic primer mtDNA genome reverse

<400> SEQUENCE: 5
cactctttac gccggcttct att                                               23

<210> SEQ ID NO 6
<211> LENGTH: 20
<212> TYPE: DNA
<213> ORGANISM: Artificial Sequence
<220> FEATURE:
<223> OTHER INFORMATION: synthetic primer TNF nuclear gene forward

<400> SEQUENCE: 6
cctgccccaa tccctttatt                                                   20

<210> SEQ ID NO 7
<211> LENGTH: 21
<212> TYPE: DNA
<213> ORGANISM: Artificial Sequence
<220> FEATURE:
<223> OTHER INFORMATION: synthetic primer TNF nuclear gene reverse

<400> SEQUENCE: 7
ggtttcgaag tggtggtctt g                                                 21

<210> SEQ ID NO 8
<211> LENGTH: 16569
<212> TYPE: DNA
<213> ORGANISM: Homo sapiens
<220> FEATURE:
<221> NAME/KEY: misc_feature
<222> LOCATION: (3107)..(3107)
<223> OTHER INFORMATION: n is a, c, g or t

<400> SEQUENCE: 8
gatcacaggt ctatcaccct attaaccact cacgggagct ctccatgcat ttggtatttt       60 cgtctgggg gtatgcacgc gatagcattg cgagacgctg gagccggagc acccctatgtc      120 gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aaccccccct ccccgcttc tggccacagc acttaaacac atctctgcca aaccccaaaa     360
```

```
acaaagaacc ctaacaccag cctaaccaga tttcaaattt tatcttttgg cggtatgcac      420
ttttaacagt caccccccaa ctaacacatt attttcccct cccactccca tactactaat      480
ctcatcaata caaccccgc ccatcctacc cagcacacac acaccgctgc taacccata        540 ccccgaacca accaaacccc aaagacaccc cccacagttt atgtagctta cctcctcaaa      600
gcaatacact gaaaatgttt agacgggctc acatcacccc ataaacaaat aggtttggtc      660
ctagcctttc tattagctct tagtaagatt acacatgcaa gcatcccgt tccagtgagt       720 tcaccctcta aatcaccacg atcaaaagga acaagcatca agcacgcagc aatgcagctc      780
aaaacgctta gcctagccac accccacgg gaaacagcag tgattaaccct ttagcaataa      840 acgaaagttt aactaagcta tactaacccc agggttggtc aatttcgtgc cagccaccgc      900
ggtcacacga ttaacccaag tcaatagaag ccggcgtaaa gagtgtttta gatcacccc      960 tccccaataa agctaaaact cacctgagtt gtaaaaaact ccagttgaca caaaatagac     1020
tacgaaagtg gctttaacat atctgaacac acaatagcta agacccaaac tgggattaga     1080
taccccacta tgcttagccc taaacctcaa cagttaaatc aacaaaactg ctcgccagaa     1140
cactacgagc cacagcttaa aactcaaagg acctggcggt gcttcatatc cctctagagg     1200
agcctgttct gtaatcgata aaccccgatc aacctcacca cctcttgctc agcctatata     1260
ccgccatctt cagcaaaccc tgatgaaggc tacaaagtaa gcgcaagtac ccacgtaaag     1320
acgttaggtc aaggtgtagc ccatgaggtg gcaagaaatg ggctacattt tctaccccag     1380
aaaactacga tagcccttat gaaacttaag ggtcgaaggt ggatttagca gtaaactaag     1440
agtagagtgc ttagttgaac agggccctga agcgcgtaca caccgcccgt caccctcctc     1500
aagtatactt caaaggacat ttaactaaaa cccctacgca tttatataga ggagacaagt     1560
cgtaacatgg taagtgtact ggaaagtgca cttggacgaa ccagagtgta gcttaacaca     1620
aagcacccaa cttacactta ggagatttca acttaacttg accgctctga gctaaaccta     1680
gccccaaacc cactccacct tactaccaga caaccttagc caaaccattt acccaaataa     1740
agtataggcg atagaaattg aaacctggcg caatagatat agtaccgcaa gggaaagatg     1800
aaaaattata accaagcata atatagcaag gactaacccc tataccttct gcataatgaa     1860
ttaactagaa ataactttgc aaggagagcc aaagctaaga ccccgaaac cagacgagct     1920 acctaagaac agctaaaaga gcacacccgt ctatgtagca aaatagtggg aagatttata     1980
ggtagaggcg acaaacctac cgagcctggt gatagctggt tgtccaagat agaatcttag     2040 ttcaactta aatttgccca cagaaccctc taaatcccct tgtaaattta actgttagtc     2100
caaagaggaa cagctctttg gacactagga aaaaccttg tagagagagt aaaaaattta     2160
acacccatag taggcctaaa agcagccacc aattaagaaa gcgttcaagc tcaacaccca     2220
ctacctaaaa aatcccaaac atataactga actcctcaca cccaattgga ccaatctatc     2280
accctataga agaactaatg ttagtataag taacatgaaa acattctcct ccgcataagc     2340
ctgcgtcaga ttaaaacact gaactgacaa ttaacagccc aatatctaca atcaaccaac     2400
aagtcattat taccctcact gtcaacccaa cacaggcatg ctcataagga aaggttaaaa     2460
aaagtaaaag gaactcggca aatcttaccc cgcctgttta ccaaaaacat cacctctagc     2520
atcaccagta ttagaggcac cgcctgccca gtgacacatg tttaacggcc gcggtaccct     2580
aaccgtgcaa aggtagcata atcacttgtt ccttaaatag ggacctgtat gaatggctcc     2640
acgagggttc agctgtctct tactttaac cagtgaaatt gacctgcccg tgaagaggcg     2700
```

-continued

```
ggcataacac agcaagacga gaagacccta tggagcttta atttattaat gcaaacagta    2760
cctaacaaac ccacaggtcc taaactacca aacctgcatt aaaaatttcg gttggggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctacnttc aaattcctcc    3120
ctgtacgaaa ggacaagaga ataaggcct acttcacaaa gcgccttccc ccgtaaatga     3180
tatcatctca acttagtatt atacccacac ccacccaaga cagggtttg ttaagatggc     3240 agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac ccaacccct ggtcaacctc     3600 aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aaccccttc     3900 gaccttgccg aaggggagtc cgaactagtc tcaggcttca acatcgaata cgccgcaggc    3960
cccttcgccc tattcttcat agccgaatac acaaacatta ttataataaa caccctcacc    4020
actacaatct tcctaggaac aacatatgac gcactctccc ctgaactcta cacaacatat    4080
tttgtcacca agaccctact tctaacctcc ctgttcttat gaattcgaac agcatacccc    4140
cgattccgct acgaccaact catacacctc ctatgaaaaa acttcctacc actcacccta    4200
gcattactta tatgatatgt ctccataccc attacaatct ccagcattcc ccctcaaacc    4260
taagaaatat gtctgataaa agagttactt tgatagagta ataataggag cttaaacccc    4320
ccttatttct aggactatga gaatcgaacc catccctgag aatccaaaat tctccgtgcc    4380
acctatcaca ccccatccta aagtaaggtc agctaaataa gctatcgggc ccataccccg    4440
aaaatgttgg ttatacccctt ccgtactaa ttaatcccct ggcccaaccc gtcatctact    4500
ctaccatctt tgcaggcaca ctcatcacag cgctaagctc gcactgattt tttacctgag    4560
taggcctaga aataaacatg ctagctttta ttccagttct aaccaaaaaa ataaaccctc    4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagcccct    4800 ttcacttctg agtcccagag gttacccaag gcacccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
```

```
taactactac cgcattccta ctactcaact taaactccag caccacgacc ctactactat    5160
ctcgcacctg aaacaagcta acatgactaa caccccttaat tccatccacc ctcctctccc   5220
taggaggcct gccccccgcta accggctttt tgcccaaatg gccattatc gaagaattca    5280 caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aacccacccc attcctcccc acactcatcg    5460
cccttaccac gctactccta cctatctccc cttttatact aataatctta tagaaattta    5520 ggttaaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaaagaggcc taaccccttgt ctttagattt acagtccaat gcttcactca    5880 gccatttttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacccca    6120 tcataatcgg aggctttggc aactgactag ttccccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccaccct ggagcctccg tagacctaac catcttctcc ttacacctag    6360
caggtgtctc ctctatctta ggggccatca atttcatcac aacaattatc aatataaaaac    6420 cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgacccccg ccggaggagg agaccccatt ctataccaac    6600
acctattctg attttttcggt caccctgaag tttatattct tatcctacca ggcttcggaa    6660
taatctccca tattgtaact tactactccg gaaaaaaaga accattttgga tacataggta    6720 tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagccctag gattcatctt tcttttcacc gtaggtggcc    6960
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttcccta ttctcaggct acaccctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccaccctacc acacattcga agaacccgta tacataaaat    7440
```

```
ctagacaaaa aaggaaggaa tcgaacccccc caaagctggt ttcaagccaa ccccatggcc      7500
tccatgactt tttcaaaaag gtattagaaa aaccatttca taactttgtc aaagttaaat      7560
tataggctaa atcctatata tcttaatggc acatgcagcg caagtaggtc tacaagacgc      7620
tacttcccct atcatagaag agcttatcac ctttcatgat cacgccctca taatcatttt      7680
ccttatctgc ttcctagtcc tgtatgccct tttcctaaca ctcacaacaa aactaactaa      7740
tactaacatc tcagacgctc aggaaataga aaccgtctga actatcctgc ccgccatcat      7800
cctagtcctc atcgccctcc catccctacg catcctttac ataacagacg aggtcaacga      7860 tcccctccctt accatcaaat caattggcca ccaatggtac tgaacctacg agtacaccga      7920
ctacggcgga ctaatcttca actcctacat acttccccca ttattcctag aaccaggcga      7980
cctgcgactc cttgacgttg acaatcgagt agtactcccg attgaagccc ccattcgtat      8040
aataattaca tcacaagacg tcttgcactc atgagctgtc cccacattag gcttaaaaac      8100
agatgcaatt cccggacgtc taaaccaaac cactttcacc gctacacgac cgggggtata      8160
ctacggtcaa tgctctgaaa tctgtggagc aaaccacagt ttcatgccca tcgtcctaga      8220
attaattccc ctaaaaatct ttgaaatagg gcccgtattt accctatagc accccctcta      8280
ccccctctag agcccactgt aaagctaact tagcattaac cttttaagtt aaagattaag      8340
agaaccaaca cctctttaca gtgaaatgcc ccaactaaat actaccgtat ggcccaccat      8400
aattaccccc atactcctta cactattcct catcacccaa ctaaaatat taaacacaaa      8460 ctaccaccta cctccctcac caaagcccat aaaaataaaa aattataaca aaccctgaga      8520
accaaaatga cgaaaatct gttcgcttca ttcattgccc ccacaatcct aggcctaccc      8580
gccgcagtac tgatcattct atttccccct ctattgatcc ccacctccaa atatctcatc      8640
aacaaccgac taatcaccac ccaacaatga ctaatcaaac taacctcaaa acaaatgata      8700
accatacaca cactaaagg acgaacctga tctcttatac tagtatcctt aatcattttt      8760
attgccacaa ctaacctcct cggactcctg cctcactcat ttacaccaac cacccaacta      8820
tctataaacc tagccatggc catcccctta tgagcgggca cagtgattat aggctttcgc      8880
tctaagatta aaaatgccct agcccacttc ttaccacaag gcacacctac accccttatc      8940
cccatactag ttattatcga aaccatcagc ctactcattc aaccaatagc cctggccgta      9000
cgcctaaccg ctaacattac tgcaggccac ctactcatgc acctaattgg aagcgccacc      9060
ctagcaatat caaccattaa ccttccctct acacttatca tcttcacaat tctaattcta      9120
ctgactatcc tagaaatcgc tgtcgcctta atccaagcct acgttttcac acttctagta      9180
agcctctacc tgcacgacaa cacataatga cccaccaatc acatgcctat catatagtaa      9240
aacccagccc atgacccta acaggggccc tctcagccct cctaatgacc tccggcctag      9300
ccatgtgatt tcacttccac tccataacgc tcctcatact aggcctacta accaacacac      9360
taaccatata ccaatgatgg cgcgatgtaa cacgagaaag cacataccaa ggccaccaca      9420
caccacctgt ccaaaaaggc cttcgatacg ggataatcct atttattacc tcagaagttt      9480
ttttcttcgc aggatttttc tgagcctttt accactccag cctagcccct accccccaat      9540
taggagggca ctggccccca acaggcatca ccccgctaaa tcccctagaa gtcccactcc      9600
taaacacatc cgtattactc gcatcaggag tatcaatcac ctgagctcac catagtctaa      9660
tagaaaacaa ccgaaaccaa ataattcaag cactgcttat tacaatttta ctgggtctct      9720 attttacccct cctacaagcc tcagagtact tcgagtctcc cttcaccatt tccgacggca      9780
tctacggctc aacatttttt gtagccacag gcttccacgg acttcacgtc attattggct      9840
```

```
caactttcct cactatctgc ttcatccgcc aactaatatt tcactttaca tccaaacatc   9900
actttggctt cgaagccgcc gcctgatact ggcattttgt agatgtggtt tgactatttc   9960
tgtatgtctc catctattga tgagggtctt actcttttag tataaatagt accgttaact  10020
tccaattaac tagttttgac aacattcaaa aagagtaat aaacttcgcc ttaattttaa  10080
taatcaacac cctcctagcc ttactactaa taattattac attttgacta ccacaactca  10140
acggctacat agaaaaatcc acccct tacg agtgcggctt cgaccctata tcccccgccc  10200
gcgtcccttt ctccataaaa ttcttcttag tagctattac cttcttatta tttgatctag  10260
aaattgccct ccttttaccc ctaccatgag ccctacaaac aactaacctg ccactaatag  10320
ttatgtcatc cctcttatta atcatcatcc tagccctaag tctggcctat gagtgactac  10380
aaaaaggatt agactgaacc gaattggtat atagtttaaa caaaacgaat gatttcgact  10440
cattaaatta tgataatcat atttaccaaa tgccctcat ttacataaat attatactag  10500
catttaccat ctcacttcta ggaatactag tatatcgctc acctcata tcctccctac  10560
tatgcctaga aggaataata ctatcgctgt tcattatagc tactctcata accctcaaca  10620
cccactccct cttagccaat attgtgccta ttgccatact agtctttgcc gcctgcgaag  10680
cagcggtggg cctagcccta ctagtctcaa tctccaacac atatggccta gactacgtac  10740
ataacctaaa cctactccaa tgctaaaact aatcgtccca acaattatat tactaccact  10800
gacatgactt ccaaaaaac acataatttg aatcaacaca accacccaca gcctaattat  10860
tagcatcatc cctctactat ttttttaacca aatcaacaac aacctattta gctgttcccc  10920
aaccttttcc tccgaccccc taacaaccccc cctcctaata ctaactacct gactcctacc  10980
cctcacaatc atggcaagcc aacgccactt atccagtgaa ccactatcac gaaaaaaact  11040
ctacctctct atactaatct ccctacaaat ctccttaatt ataacattca cagccacaga  11100
actaatcata ttttatatct tcttcgaaac cacacttatc cccaccttgg ctatcatcac  11160
ccgatgaggc aaccagccag aacgcctgaa cgcaggcaca tacttcctat tctacaccct  11220
agtaggctcc cttccctac tcatcgcact aatttacact cacaacacccc taggctcact  11280
aaacattcta ctactcactc tcactgccca agaactatca aactcctgag ccaacaactt  11340
aatatgacta gcttacacaa tagcttttat agtaaagata cctctttacg gactccactt  11400
atgactccct aaagcccatg tcgaagcccc catcgctggg tcaatagtac ttgccgcagt  11460
actcttaaaa ctaggcggct atggtataat acgcctcaca ctcattctca accccctgac  11520
aaaacacata gcctacccct tccttgtact atccctatga ggcataatta taacaagctc  11580
catctgccta cgacaaacag acctaaaatc gctcattgca tactcttcaa tcagccacat  11640
agccctcgta gtaacagcca ttctcatcca accccctga agcttcaccg gcgcagtcat  11700
tctcataatc gcccacgggc ttacatcctc attactattc tgcctagcaa actcaaacta  11760
cgaacgcact cacagtcgca tcataatcct ctctcaagga cttcaaactc tactcccact  11820
aatagctttt tgatgacttc tagcaagcct cgctaacctc gccttacccc ccactattaa  11880
cctactggga gaactctctg tgctagtaac cacgttctcc tgatcaaaata tcactctcct  11940
acttacagga ctcaacatac tagtcacagc cctatactcc ctctacatat ttaccacaac  12000
acaatggggc tcactcaccc accacattaa caacataaaa ccctcattca cacgagaaaa  12060
caccctcatg ttcatacacc tatccccat tctcctccta tccctcaacc ccgacatcat  12120
taccgggttt tcctcttgta aatatagttt aaccaaaaca tcagattgtg aatctgacaa  12180
```

-continued

```
cagaggctta cgacccctta tttaccgaga aagctcacaa gaactgctaa ctcatgcccc    12240
catgtctaac aacatggctt tctcaacttt taaaggataa cagctatcca ttggtcttag    12300
gccccaaaaa ttttggtgca actccaaata aaagtaataa ccatgcacac tactataacc    12360
accctaaccc tgacttccct aattccccca atccttacca ccctcgttaa ccctaacaaa    12420
aaaaactcat accccccatta tgtaaaatcc attgtcgcat ccacctttat tatcagtctc    12480
ttccccacaa caatattcat gtgcctagac caagaagtta ttatctcgaa ctgacactga    12540
gccacaaccc aaacaaccca gctctcccta agcttcaaac tagactactt ctccataata    12600
ttcatccctg tagcattgtt cgttacatgg tccatcatag aattctcact gtgatatata    12660
aactcagacc caaacattaa tcagttcttc aaatatctac tcatcttcct aattaccata    12720
ctaatcttag ttaccgctaa caacctattc caactgttca tcggctgaga gggcgtagga    12780
attatatcct tcttgctcat cagttgatga tacgcccgag cagatgccaa cacagcagcc    12840
attcaagcaa tcctatacaa ccgtatcggc gatatcggtt tcatcctcgc cttagcatga    12900
tttatcctac actccaactc atgagaccca caacaaatag cccttctaaa cgctaatcca    12960
agcctcaccc cactactagg cctcctccta gcagcagcag gcaaatcagc ccaattaggt    13020
ctccacccct gactccccte agccatagaa ggccccaccc cagtctcagc cctactccac    13080
tcaagcacta tagttgtagc aggaatcttc ttactcatcc gcttccaccc cctagcagaa    13140
aatagcccac taatccaaac tctaacacta tgcttaggcg ctatcaccac tctgttcgca    13200
gcagtctgcg cccttacaca aaatgacatc aaaaaaatcg tagccttctc cacttcaagt    13260
caactaggac tcataatagt tacaatcggc atcaaccaac cacacctagc attcctgcac    13320
atctgtaccc acgccttctt caaagccata ctatttatgt gctccgggtc catcatccac    13380
aaccttaaca atgaacaaga tattcgaaaa ataggaggac tactcaaaac catacctctc    13440
acttcaacct ccctcaccat tggcagccta gcattagcag gaatacccttt cctcacaggt    13500 ttctactcca aagaccacat catcgaaacc gcaaacatat catacacaaa cgcctgagcc    13560
ctatctatta ctctcatcgc tacctccctg acaagcgcct atagcactcg aataattctt    13620
ctcaccctaa caggtcaacc tcgcttcccc acccttacta acattaacga aaataacccc    13680
accctactaa accccattaa acgcctggca gccggaagcc tattcgcagg atttctcatt    13740
actaacaaca tttcccccgc atccccctte caaacaacaa tccccctcta cctaaaactc    13800
acagccctcg ctgtcacttt cctaggactt ctaacagccc tagacctcaa ctacctaacc    13860
aacaaactta aaataaaatc cccactatgc acatttttatt tctccaacat actcggattc    13920
taccctagca tcacacaccg cacaatcccc tatctaggcc ttcttacgag ccaaaacctg    13980
cccctactcc tcctagacct aacctgacta gaaaagctat tacctaaaac aatttcacag    14040
caccaaatct ccacctccat catcacctca acccaaaaag gcataattaa actttacttc    14100
ctctctttct tcttcccact catcctaacc ctactcctaa tcacataacc tattcccccg    14160
agcaatctca attacaatat atacaccaac aaacaatgtt caaccagtaa ctactactaa    14220
tcaacgccca taatcataca aagcccccgc accaatagga tcctcccgaa tcaaccctga    14280 ccctctcct tcataaatta ttcagcttcc tacactatta agtttaccac aaccaccac    14340 cccatcatac tctttcaccc acagcaccaa tcctacctcc atcgctaacc ccactaaaac    14400
actcaccaag acctcaaccc ctgaccccca tgcctcagga tactcctcaa tagccatcgc    14460
tgtagtatat ccaaagacaa ccatcattcc ccctaaataa attaaaaaaa ctattaaacc    14520 catataaccct cccccaaaat tcagaataat aacacacccg accacaccgc taacaatcaa    14580
```

```
tactaaaccc ccataaatag gagaaggctt agaagaaaac cccacaaacc ccattactaa    14640
acccacactc aacagaaaca aagcatacat cattattctc gcacggacta caaccacgac    14700
caatgatatg aaaaaccatc gttgtatttc aactacaaga acaccaatga ccccaatacg    14760
caaaactaac cccctaataa aattaattaa ccactcattc atcgacctcc caccccatc     14820 caacatctcc gcatgatgaa acttcggctc actccttggc gcctgcctga tcctccaaat    14880
caccacagga ctattcctag ccatgcacta ctcaccagac gcctcaaccg ccttttcatc    14940
aatcgcccac atcactcgag acgtaaatta tggctgaatc atccgctacc ttcacgccaa    15000
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggcacagt     15180 aattacaaac ttactatccg ccatcccata cattgggaca gacctagttc aatgaatctg    15240
aggaggctac tcagtagaca gtcccaccct cacacgattc tttacctttc acttcatctt    15300
gcccttcatt attgcagccc tagcaacact ccacctccta ttcttgcacg aaacgggatc    15360 aaacaaccc ctaggaatca cctcccattc cgataaaatc accttccacc cttactacac     15420
aatcaaagac gccctcggct tacttctctt ccttctctcc ttaatgacat taacactatt    15480
ctcaccagac ctcctaggcg acccagacaa ttatacccta gccaacccct taaacaccc     15540 tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcacttta    15720
ttgactccta gccgcagacc tcctcattct aacctgaatc ggaggacaac cagtaagcta    15780
cccttttacc atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaaccggag atgaaaacct ttttccaagg acaaatcaga    15960
gaaaaagtct ttaactccac cattagcacc caaagctaag attctaattt aaactattct    16020
ctgttctttc atggggaagc agatttgggt accacccaag tattgactca cccatcaaca    16080
accgctatgt atttcgtaca ttactgccag ccaccatgaa tattgtacgg taccataaat    16140
acttgaccac ctgtagtaca taaaaaccca atccacatca aaaccccctc ccatgctta    16200 caagcaagta cagcaatcaa ccctcaacta tcacacatca actgcaactc caaagccacc    16260
cctcacccac taggatacca acaaacctac ccaccttaa cagtacatag tacataaagc     16320
catttaccgt acatagcaca ttacagtcaa atcccttctc gtccccatgg atgaccccc     16380 tcagataggg gtcccttgac caccatcctc cgtgaaatca atatcccgca caagagtgct    16440
actctcctcg ctccgggccc ataacacttg ggggtagcta aagtgaactg tatccgacat    16500
ctggttccta cttcagggtc ataaagccta aatagcccac acgttcccct taaataagac    16560
atcacgatg                                                            16569
```

<210> SEQ ID NO 9
<211> LENGTH: 22
<212> TYPE: DNA
<213> ORGANISM: Artificial Sequence
<220> FEATURE:
<223> OTHER INFORMATION: synthetic primer forward 3.4 kb deleted
      sequence

<400> SEQUENCE: 9

```
cccactcatc acctaaacct ac                                              22

<210> SEQ ID NO 10
<211> LENGTH: 20
<212> TYPE: DNA
<213> ORGANISM: Artificial Sequence
<220> FEATURE:
<223> OTHER INFORMATION: synthetic primer reverse 3.4 kb deleted
      sequence

<400> SEQUENCE: 10
ggtaggagtc aggtagttag                                                 20
```